United States Patent [19]
Lednicer

[11] 3,965,180
[45] June 22, 1976

[54] 4'-FLUORO-4- [4-(PHENYL)-4-ALKOXY-CYCLOHEXYL]AMINO BUTYROPHENONES AND THE SALTS THEREOF

[75] Inventor: Daniel Lednicer, Portage, Mich.

[73] Assignee: The Upjohn Company, Kalamazoo, Mich.

[22] Filed: Feb. 20, 1973

[21] Appl. No.: 333,896

Related U.S. Application Data

[63] Continuation-in-part of Ser. No. 194,530, Nov. 1, 1971, abandoned.

[52] U.S. Cl. .................. 260/570.5 CA; 260/239 B; 260/247.7 Z; 260/268 R; 260/793.83; 260/295.5 S; 260/326.5 R; 260/340.7; 260/349; 260/456 R; 260/456 P; 260/501.12; 260/501.18; 260/562 A; 260/566 A; 260/566 AC; 260/570 R; 260/570.5 C; 260/540 R; 260/611 A; 260/618 R; 424/244; 424/250; 424/266; 424/267; 424/274; 424/316; 424/330
[51] Int. Cl.² ...................................... C07C 98/065
[58] Field of Search ................. 260/570.5 C, 295.55, 260/570.5 CA, 581.12, 501.18

[56] References Cited
UNITED STATES PATENTS 3,109,845  11/1963  Seeger et al. ................. 260/570.5 X
3,467,705   9/1969  Gigante et al. ............... 260/570.5 X

FOREIGN PATENTS OR APPLICATIONS 2,142,480  3/1972  Germany ........................ 260/570.5

Primary Examiner—Robert V. Hines
Attorney, Agent, or Firm—John T. Reynolds; William Hodes

[57] ABSTRACT

This invention relates to novel 4-(substituted alkoxy)-4-(substituted phenyl)cyclohexylamines embraced by the formula

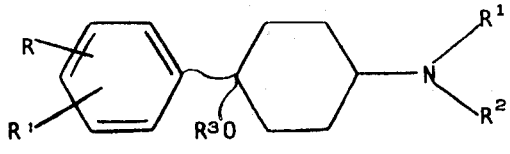

wherein ~ is a generic expression denoting cis and trans stereoconfiguration and mixtures thereof, with the proviso that when the stereoconfiguration of the linkage connecting the cyclohexane ring and $R^3O$ is cis to the amino group, the linkage connecting the cyclohexane and phenyl rings is always trans, and vice versa; R is selected from the group consisting of lower alkyl of 1 through 4 carbon atoms, chlorine, fluorine, bromine, trifluoromethyl, and lower alkoxy of 1 through 4 carbon atoms; R' has the same meaning as R and in addition hydrogen; $R^1$ is selected from the group consisting of hydrogen and lower alkyl of 1 through 4 carbon atoms; $R^2$ is selected from the group consisting of hydrogen, lower alkyl of 1 through 4 carbon atoms, ring monosubstituted aroylalkyl wherein the substituents have the same meaning as R and R', above, aryl is from 6 through 10 carbon atoms and alkyl of from 1 through 4 carbon atoms and bis (ring monosubstituted)arylalkyl wherein the substituents have the same meaning as R and R', above, aryl is from 6 through 10 carbon atoms and alkyl of from 1 through 4 carbon atoms; $R^1$ and $R^2$ taken together with -N< is a saturated heterocyclic amino radical selected from the group consisting of unsubstituted and monosubstituted pyrrolidino, piperidino, hexamethyleneimino, morpholino and piperazino; $R^3$ is lower alkyl of 1 through 4 carbon atoms; and an acid addition salt thereof. It also relates to intermediates and processes for the preparation of the aforesaid novel compounds (1) and novel derivatives thereof. The systemic administration to humans and animals of the novel compounds (1) depresses their central nervous systems.

13 Claims, No Drawings

4'-FLUORO-4-[4-(PHENYL)-4-ALKOXY-CYCLOHEXYL]AMINO BUTYROPHENONES AND THE SALTS THEREOF

CROSS REFERENCE TO RELATED APPLICATIONS

This application is a continuation-in-part of co-pending application Ser. No. 194,530, filed Nov. 1, 1971 and now abandoned.

BRIEF SUMMARY OF THE INVENTION

The novel compounds of this invention, intermediates therefor and processes for their production are illustratively represented by the following sequence of formulae

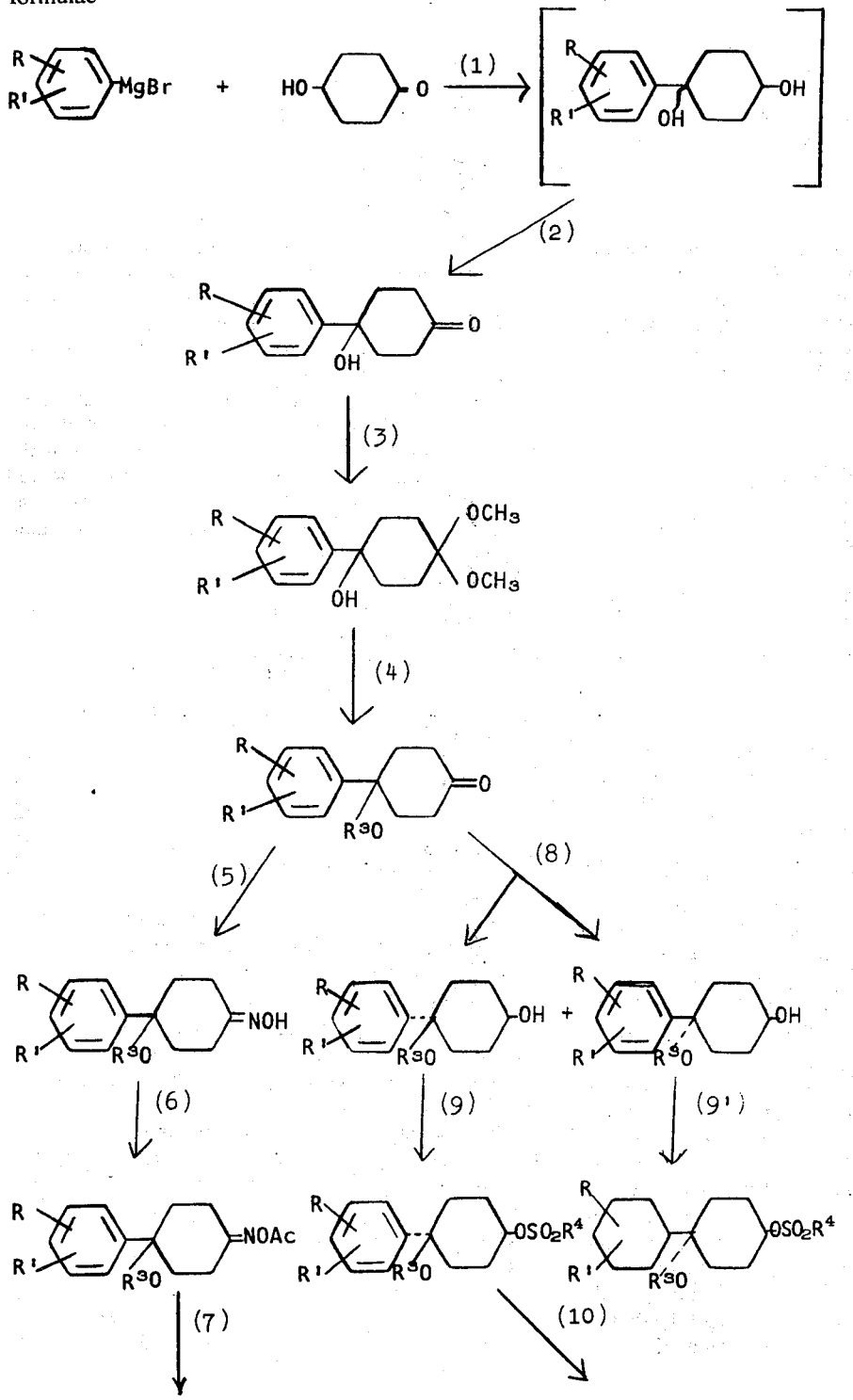

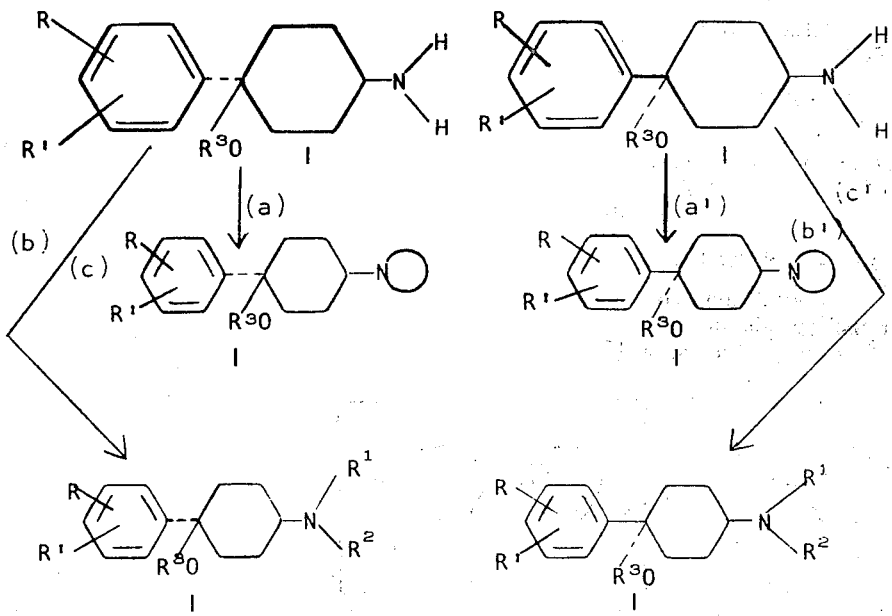

wherein (, R, R', R¹, R² and R³ have the same meaning as above, R⁴ is selected from the group consisting of alkyl of from 1 through 3 carbon atoms and aryl of from 6 through 10 carbon atoms, Ac is the acyl radical of 1 hydrocarbon carboxylic acid containing from 1 through 3 carbon atoms, and the symbol

−N⟩ represents a saturated amino radical selected from the group consisting of unsubstituted and monosubstituted pyrrolidino, piperidino, hexamethyleneimino, morpholino and piperazino.

Examples of lower alkoxy of from one through four carbon atoms are methoxy, ethoxy, propoxy and butoxy and the isomeric forms thereof. Examples of alkyl of from one through four carbon atoms are methyl, ethyl, propyl and butyl and the isomeric forms thereof. Examples of acyl of from one through three carbon atoms are formyl, acetyl and propionyl. Examples of aryl of from six through ten carbon atoms are benzene, toluene and naphthalene. Examples of ring monosubstituted aroylalkyl wherein the substituents are selected from the group consisting of hydrogen, alkyl of from one through four carbon atoms, fluorine, chlorine, bromine, trifluoromethyl and alkoxy of from one through four carbon atoms, aryl is from six through ten carbon atoms and alkyl is from one through six carbon atoms are 4-oxo-4-(p-fluorophenyl)butyl, 4-oxo-4-(2-chloro-1-methylphenyl)-butyl, 4-oxo-4-(o-propoxy-α-naphthyl)butyl, 2-oxo-(m-ethyl-α-naphthyl)ethyl, 3-oxo-3-(p-trifluoromethylphenyl)propyl, 5-oxo-5-(o-ethoxyphenyl)pentyl, and the isomeric forms thereof. Examples of bis (ring monosubstituted) arylalkyl wherein the substituents are selected from the group consisting of hydrogen, alkyl of from one through four carbon atoms, fluorine, chlorine, bromine, trifluoromethyl and alkoxy of from one through four carbon atoms, aryl is from six through ten carbon atoms and alkyl is from one through six carbon atoms are 4,4-bis(p-fluorophenyl)butyl, 4,4-bis(1,3-dimethylphenyl)-butyl, 4,4-bis(4-chloro-1-methylphenyl)butyl, 2,2-bis(m-ethoxy-α-naphthyl)ethyl, 4,4-bis(p-tolyl)butyl, 3,3-bis(o-trifluoromethylphenyl)propyl and the isomeric forms thereof. Examples of unsubstituted and monosubstituted pyrrolidino, piperidino, hexamethylimino, morpholino and piperazino are pyrrolidino, 2-methylpyrrolidino, 2-ethylpiperidino, hexamethylenimino, 3-methoxyhexamethylenimino, morpholino, 2-methylmorpholino, 2-ethoxymorpholino, piperazino, 2-methylpiperazino and 3-isopropylpiperazino.

The novel 4-(substituted alkoxy)-(substituted phenyl)-cyclohexylamines of Formula I exist either in the nonprotonated (free base) form or in the protonated (acid addition salt) form, depending on the pH of the environment. They form stable protonates, i.e., acid addition salts, on neutralization of the free base form with suitable acids, for example, hydrochloric, hydrobromic, sulfuric, phosphoric, nitric, acetic, propionic, palmitic, benzoic, salicylic, hexynoic, phenylbutyric, naphthoic, glycolic, succinic, nicotinic, tartaric, maleic, malic, pamoic, methanesulfonic, cyclohexanesulfonic, citric and lactic acids, and the like. Conversely, the free base of the novel compounds of Formula I can be obtained from a salt (e.g., from the hydrochloride or sulfate salts) by neutralization with a base such as sodium hydroxide, extracting with an immiscible solvent, for example chloroform, drying the extract, for example with anhydrous sodium sulfate, and removing the solvent by evaporation.

The compounds embraced by Formula I of the flowsheet, above, are prepared by the procedures indicated therein, employing the methods and reactions described below.

1. The first step of the process for preparing the compounds first designated I in the above flow-sheet, i.e., the 4-(substituted alkoxy)-4-(substituted phenyl)-cyclohexylamines wherein R¹ and R² are hydrogen, involves mixing a cooled substituted phenylmagnesium halide Grignard reagent (prepared in known manner) with the known 4-hydroxycyclohexanone, to yield the corresponding cis and trans substituted phenyl-1,4-cyclohexanediols.

2. The next step of the process comprises oxidizing (e.g., with an oxygenated hexavalent chromium compound such as sodium or potassium chromate, or with Jones reagent (chromium trioxide-sulfuric acid) at the 1-position of the cyclohexane ring of the cis and trans substituted phenyl-1,4-cyclohexanediols produced in step (1), to yield a corresponding 4-substituted phenyl-4-hydroxycyclohexanone.

The starting substituted phenylmagnesium halide and 4-hydroxycyclohexanone can be converted directly to the corresponding substituted phenyl-4-hydroxycyclohexanone without isolation of the corresponding cis and trans substituted phenyl-1,4-cyclohexanediols prepared in step (1).

3. In order to avoid side reaction in the subsequent step, a 4-substituted phenyl-4-hydroxycyclohexanone produced in step (2) is protected by conversion to its dialkyl ketal, e.g., by allowing an alkanol solution of the compound to stand at moderate (room) temperature with trifluoroacetic acid, to yield a corresponding 4-substituted phenyl-4-hydroxycyclohexanone dialkyl ketal.

4. A 4-substituted-4-hydroxycyclohexanone dialkyl ketal obtained in step (3) is converted to a corresponding 4-alkoxide by reaction with sodium hydride, which on heating with an appropriate alkyl halide, followed by treatment with aqueous acid to deketalize, yields a corresponding 4-alkoxy-4-(substituted phenyl)cyclohexanone.

5. A 4-alkoxy-4-(substituted phenyl)cyclohexanone oxime is prepared by conventional procedures, e.g., by heating (preferably at reflux temperature) a corresponding 4-alkoxy-4-(substituted phenyl)cyclohexanone, obtained in step (4), with hydroxylamine (or a mineral acid addition salt of hydroxylamine with an alkali metal hydroxide) in a solvent such as ethanol or tetrahydrofuran.

6. In this step, a 4-alkoxy-4-(substituted phenyl)-cyclohexanone oxime resulting from step (5) is converted by conventional methods, e.g., by mixing (at moderate or low temperature) with an anhydride of a hydrocarbon carboxylic acid in the presence of an esterification catalyst such as pyridine, to a corresponding 4-alkoxy-4-(substituted phenyl)-cyclohexanone oxime acylate.

7. A 4-alkoxy-4-(substituted phenyl)cyclohexanone oxime acylate prepared in step (6) is selectively reduced, e.g., with diborane or lithium aluminum hydride, in a solvent such as tetrahydrofuran at moderate (room) temperature, to yield a corresponding 4-cis-alkoxy-4-trans-(substituted phenyl)cyclohexylamine (I) in its free base form. On treating an ether extract of a thus produced compound with a slight excess of a suitable acid, the acid addition salt form is obtained.

The free base or acid addition salt forms of the 4-cis-alkoxy-4-trans-(substituted phenyl)cyclohexylamines (the compounds first designated I in the flow-sheet, above) obtained as in step (7), can be employed as starting materials for producing a variety of derivatives thereof, for example, in accordance with the methods described, in (a) through (c) that follow.

a. Heating (e.g., under reflux) a 4-cis-alkoxy-4-trans-(substituted phenyl)cyclohexylamine (I) with a dihaloalkane gives a corresponding 1-[4-cis-alkoxy-4-trans-(substituted phenyl)cyclohexyl]nitrogen ring containing heterocyclic compound (I) where $R_1$ and $R_2$ are connected, which on dissolving in ether and treating with an ethereal solution of an appropriate acid yields the corresponding acid addition salt. For example, heating a 4-cis-alkoxy-4-trans-(substituted phenyl)cyclohexylamine (I) with 1,5-diiodopentane, 1,4-dibromobutane or 1,6-diiodohexane, yields, respectively, a corresponding 1-[4-cis-alkoxy-4-trans-(substituted phenyl)cyclohexyl]piperidine (I), 1-[4-cis-alkoxy-4-trans(substituted phenyl)cyclohexyl]pyrrolidine (I), or 1-[4-cis-alkoxy-4-trans-(substituted phenyl)cyclohexyl]-hexamethyleneimine (I), which can be converted to a corresponding acid addition salt in the manner described in the immediately preceding sentence.

b. A compound represented in the above flow-sheet by the formula

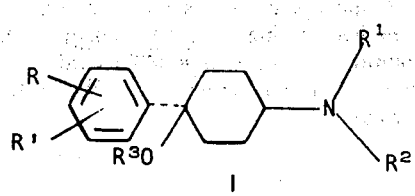

wherein R, R' and $R^1$ can have any of the meanings indicated therefor and $R^2$ is ring monosubstituted aroylalkyl wherein the substituents have the same meaning as R, aryl is from six through ten carbon atoms and alkyl is from one through six carbon atoms, can be prepared from a corresponding 4-cis-alkoxy-4-trans-(substituted phenyl)cyclohexylamine (I) by the general procedure that follows.

The process for the production of such an aroylalkyl compound selected from the group consisting of the free bases and acid addition salts of a compound of the formula

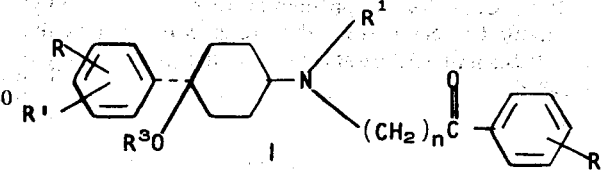

wherein R is selected from the group consisting of alkyl of from one through four carbon atoms, fluorine, chlorine, bromine, trifluoromethyl and alkoxy of from one through four carbon atoms, R' has the same meaning as R and in addition hydrogen, $R^1$ is selected from the group consisting of hydrogen and alkyl of from one through four carbon atoms and n is selected from the group consisting of the integers one through six, comprises reacting (in the presence of an alkali metal iodide and an alkali metal carbonate) a compound selected from the group consisting of the free bases and acid addition salts of a corresponding 4-cis-alkoxy-4-trans-(substituted phenyl)cyclohexylamine (I) of the formula wherein R, R' and R¹ have the same meaning as above and R² is hydrogen with a corresponding compound of the formula

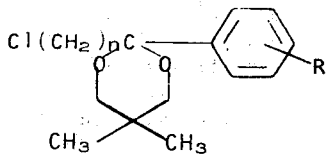

wherein R and *n* have the same meaning as above, followed by hydrolyzing (i.e., deketalizing) a thus produced compound, e.g., with aqueous acid.

c. A compound represented in the above flow-sheet by the formula

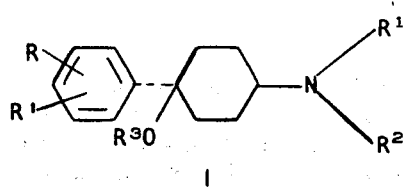

wherein R, R' and R¹ can have any of the meanings indicated therefor and R² is bis(ring monosubstituted-)arylalkyl wherein the substituents have the same meaning as R, aryl is from six through ten carbon atoms and alkyl is from one through six carbon atoms, can be prepared from a corresponding 4-cis-alkoxy-4-trans-(substituted phenyl)cyclohexylamine (I) by the general procedure that follows.

The process for the production of such an arylalkyl compound selected from the group consisting of the free bases and acid addition salts of a compound of the formula

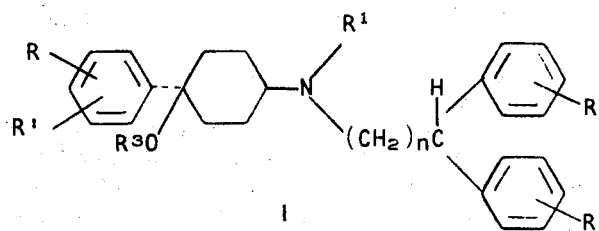

wherein R is selected from the group consisting of hydrogen, alkyl of from one through four carbon atoms, fluorine, chlorine, bromine, trifluoromethyl and alkoxy of from one through four carbon atoms, R' has the same meaning as R and in addition hydrogen, R¹ is selected from the group consisting of hydrogen and alkyl of from one through four carbon atoms and *n* is selected from the group consisting of the integers one through six, comprises reacting (in the presence of an alkali metal iodide and an alkali metal carbonate) a compound selected from the group consisting of the free bases and acid addition salts of a corresponding 4-cis-alkoxy-4-trans-(substituted phenyl)cyclohexylamine (I) of the formula

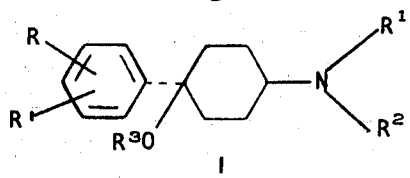

wherein R, R' and R¹ have the same meaning as above and R² is hydrogen with a corresponding compound of the formula

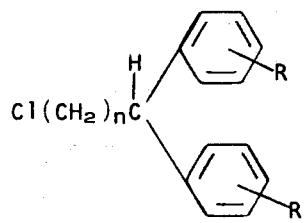

wherein R and *n* have the same meaning as above, followed by hydrolyzing (i.e., deketalizing) a thus produced compound, e.g., with aqueous acid.

8. In this step of the process, a 4-alkoxy-4-(substituted phenyl)cyclohexanone prepared in step (4) is reduced (e.g., with sodium borohydride) to give a 4-cis-alkoxy-4-trans-(substituted phenyl)cyclohexanol and a 4-trans-alkoxy-4-cis(substituted phenyl)cyclohexanol, the thus produced isomers being separated and purified by conventional procedures, such as chromatography or fractional crystallization.

9. (9') Mixing (in the cold) a 4-cis-alkoxy-4-trans-(substituted phenyl)cyclohexanol or a 4-trans-alkoxy-4-cis-(substituted phenyl)cyclohexanol prepared in step (8) in an amine base (e.g., pyridine) with an alkyl (or aryl) sulfonyl halide (such as methanesulfonyl chloride or p-toluenesulfonyl bromide), yields a corresponding 4-cis-alkoxy-4-trans-(substituted phenyl)cyclohexanol alkyl (or aryl) sulfonate or 4-trans-alkoxy-4-(substituted phenyl)cyclohexanol alkyl (or aryl) sulfonate.

10. In this step, a 4-cis-alkoxy-4-trans-(substituted phenyl)cyclohexanol alkyl (or aryl) sulfonate resulting from step (9) in a solvent such as dimethylformamide, on the addition of sodium azide, followed by heating, yields (with inversion of the stereoconfiguration) a corresponding 4-trans-alkoxy-4-cis-(substituted phenyl)cyclohexan-1-ylazide, which compound on reduction of its azide function, e.g., with lithium aluminum hydride in a solvent such as tetrahydrofuran, gives a corresponding 4-trans-alkoxy-4-cis-(substituted phenyl)cyclohexylamine (I) in its free base form. On treating an ether extract of a thus produced compound with an equivalent of an ethereal solution of a suitable acid, the acid addition salt form is obtained.

The free base or acid addition salt forms of the 4-trans-alkoxy-4-cis-(substituted phenyl)cyclohexylamines (the compounds first designated I in the flow-sheet, above) obtained as in step (10), can be employed as starting materials for producing a variety of derivatives thereof, for example, in accordance with the methods described in (a') through (c') that follow.

a'. Following the procedure of (a), above, but substituting a 4-trans-alkoxy-4-cis-(substituted phenyl)cyclohexylamine (I) as starting material, yields a corresponding 1-[4-trans-alkoxy-4-cis-(substituted phenyl)-cyclohexyl]nitrogen ring containing heterocyclic compound (I) where $R_1$ and $R_2$ are connected, or an acid addition salt thereof, e.g., 1-[4-trans-alkoxy-4-cis-(substituted phenyl)-cyclohexyl]piperidine (I), 1-[4-trans-alkoxy-4-cis-(substituted phenyl)cyclohexyl]pyrrolidine (I), 1-[4-trans-alkoxy-4-cis-(substituted phenyl)-cyclohexyl] hexamethyleneimine (I), and the like, and acid addition salts thereof.

b'. Following the procedure of (b), above, but substituting a starting material of the formula

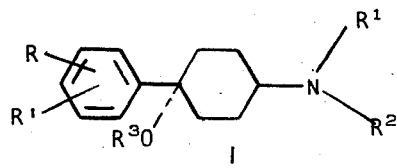

wherein R, R', $R^1$, $R^2$ and $R^3$ have the same meaning as in (b), above, yields a corresponding compound of the formula

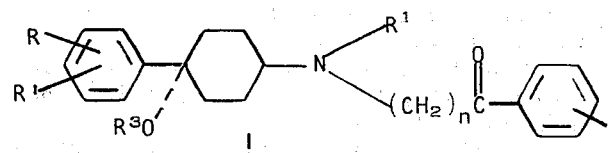

wherein R, R', $R^1$ and $n$ have the same meaning as in (b), above.

c'. Following the procedure of (c), above, but substituting a starting material of the formula

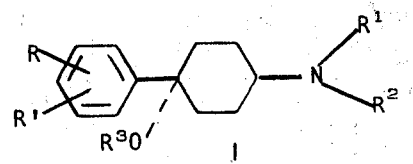

wherein R, R', $R^1$ and $R^3$ have the same meaning as in (c), above, yields a corresponding compound of the formula

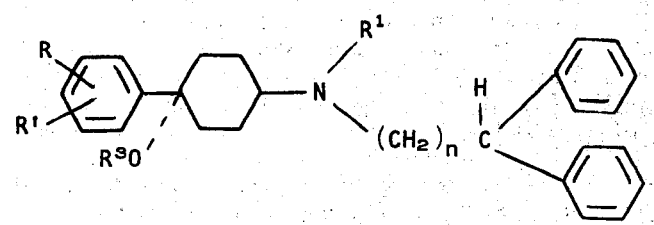

wherein R, R', $R^1$ and $n$ have the same meaning as in (c), above.

All of the compounds included within Formula I of the flow-sheet, above, can be isolated from their respective reaction mixtures by conventional means, for example, when a water-miscible solvent is used, by pouring the reaction mixture into water and separating the resulting precipitate by filtration or by extraction with water-immiscible solvents. Additional purification of the products can be accomplished by conventional means, for example, by elution chromatography from an adsorbent column with a suitable solvent such as acetone, ethyl acetate, ether, methylene chloride and Skellysolve B (hexanes), mixtures and combinations of these solvents; also by gradient elution chromatography from an adsorbent column with a suitable mixture of solvents, such as, methylene chloride-Skellysolve B, acetone-Skellysolve B, and the like.

The free bases and acid addition salts of the novel compounds of Formula I are useful as central nervous system (CNS) depressants when administered to humans and animals. They possess tranquilizing activity and are consequently useful in humans for controlling anxiety and schizophrenia; in animals the aforesaid compounds are useful for their calming effects and can be given to reduce anxiety and reduce aggressive behavior. These compounds have been shown to possess CNS depressing activity via the loss of righting reflex, traction, chimney, dish and pedestal tests carried out in the manner described by Boissier et al. in Medicina Experimentalis 4, 145 (1961).

Tranquilizing effects of certain compounds of this invention are shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves a standard pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1)

running convulsions followed by (2) tonic extensor fits; followed by (3) death.

The following compounds typical of this invention have (by intraperitoneal injection) $ED_{50}$ as shown in the table below.

| COMPOUND | $ED_{50}$ (in mg./kg.) | | | |
|---|---|---|---|---|
| | Ch | D | P | Ni |
| 4'-fluoro-4- {[4-trans-(p-fluorophenyl)-4-cis-methoxycyclohexyl]amino} butyrophenone hydrochloride (I) | 2.5 | 0.09 | 1.3 | 0.4 |
| 4'-fluoro-4- {[4-cis-methoxy-4-trans-(p-methylphenyl)cyclohexylamino} butyrophenone hydrochloride (I) | 2.5 | 1.1 | 2 | 4.5 |
| 4'-fluoro-4- {[4-cis-(p-fluorophenyl)-4-trans-methoxycyclohexyl]amino} butyrophenone hydrochloride (I) | 8 | 1.6 | 2.5 | 3.2 |

Ch = chimney test
D = dish test
P = pedestal test
Ni = nicotine antagonism
(3) test The compounds of Formula I of the invention can be prepared and administered to humans, mammals, birds and animals, in a wide variety of oral or parenteral dosage forms, singly or in admixture with other coacting compounds, in single or divided doses of from 20 mg. to 1000 mg./kg., depending on the severity of the condition being treated and the recipient's response to the medication. They can be administered with a pharmaceutical carrier which can be a solid material or a liquid in which the compound is dissolved, dispersed or suspended. The solid compositions can take the form of tablets, powders, capsules, pills, or the like, preferably in unit dosage forms for simple administration or precise dosages. The liquid compositions can take the form of solutions, emulsions, suspensions, syrups or elixirs.

DETAILED DESCRIPTION

The following examples describe the manner and process of making and using the invention and set forth the best method contemplated by the inventor of carrying out his invention, but are not construed as limiting the scope thereof.

EXAMPLE 1 cis and trans
1-(p-methoxyphenyl)-1,4-cyclohexanediol

To an ice cooled solution of p-methoxyphenylmagnesium bromide (prepared from 13.5 g. p-bromoanisole and 1.75 g. of magnesium in 100 ml. of tetrahydrofuran; there is added 2.75 g. of 4-hydroxycyclohexanone [obtained as in J. Chem. Soc. 10 (1940)] in 30 ml. of tetrahydrofuran. Following 17 hours of standing at room temperature, 50 ml. of a saturated solution of ammonium chloride is added. The organic layer is washed with water and brine and taken to dryness. The residue is suspended in 50 ml. of Skellysolve B and the solid collected on a filter. Two recrystallizations from ethyl acetate give 1.14 g. of 1-(p-methoxyphenyl)-1,4-cyclohexanediol, melting at 155° to 158° C.

Anal. Calcd. for $C_{13}H_{18}O_3$: C, 70.24; H, 8.16. Found: C, 70.05; H, 7.95.

The mother liquors are combined, taken to dryness and chromatographed on 400 ml. of Florisil (synthetic magnesium silicate) and eluted with 10% acetone in Skellysolve B. The crystalline fractions are combined and recrystallized from Skellysolve B to yield 0.46 g. of the isomeric 1-(p-methoxyphenyl)-1,4-cyclohexanediol, melting at 108.5° to 110° C.

Anal. Calcd. for $C_{13}H_{18}O_3$: C, 70.24; H, 8.16. Found: C, 70.30; H, 8.92.

EXAMPLE 2 cis and trans 1-(p-fluorophenyl)-1,4-cyclohexanediol

A solution of 5.7 g. of 4-hydroxycyclohexanone in 60 ml. of tetrahydrofuran is added to 0.1 mole of p-fluorophenylmagnesium bromide in 170 ml. of tetrahydrofuran. Following 17 hours of standing at room temperature 50 ml. of a saturated solution of ammonium chloride is added. The organic layer is washed with water and brine and taken to dryness. The residue is chromatographed over 500 ml. of Florisil. Elution with 5% acetone:Skellysolve B gives 0.65 g. of dehydrated product, melting at 60° to 70° C. Elution with 20% acetone:Skellysolve B gives a series of crystalline fractions which are combined, based on thin layer chromatography (TLC), to form two fractions. The first material is recrystallized from acetone:benzene to give 0.94 g. of 1-(p-fluorophenyl)-1,4-cyclohexanediol, melting at 113° to 115° C.

Anal. Calcd. for $C_{12}H_{15}FO_2$: C, 68.55; H, 7.19. Found: C, 68.58; H, 7.38.

The more polar material is recrystallized from ethyl acetate to give 1.5 g. of isomeric 1-(p-fluorophenyl)-1,4-cyclohexanediol, m.p. 175° to 177° C.

Anal. Calcd. for $C_{12}H_{15}FO_2$: C, 68.55; H, 7.19. Found: C, 68.04; H, 7.68.

Following the procedure of Example 2 but substituting p-methylphenylmagnesium bromide, p-chloromethylphenyl-magnesium bromide, p-trifluoromethylmagnesium bromide, and the like, yields, respectively, both the cis and trans forms of 1-(p-methylphenyl)-1,4-cyclohexanediol, 1-(p-chlorophenyl)-1,4-cyclohexanediol, 1-(p-trifluoromethylphenyl)-1,4-cyclohexanediol, and the like.

EXAMPLE 3 cis and trans
1-(2-chloro-6-methyl)phenyl-1,4-cyclohexanediol

Following the procedure of Example 1 but substituting 2-chloro-6-methylphenylmagnesium bromide [prepared from 1-bromo-2-chloro-6-methylbenzene (obtained as in J. Chem. Soc. 105, page 1907) and magnesium] yields cis and trans 1-(2-chloro-6-methyl)phenyl-1,4-cyclohexanediol.

EXAMPLE 4 cis and trans
1-(5-chloro-3-methylphenyl)-1,4-cyclohexanediol

Following the procedure of Example 1 but substituting 5-chloro-3-methylphenyl magnesium bromide [prepared from 1-bromo-5-chloro-3-methylbenzene (obtained as in J. Chem. Soc. 105, page 1907) and magnesium], yields, cis and trans 1-(5-chloro-3-methylphenyl)-1,4-cyclohexanediol.

EXAMPLE 5 cis and trans 1-(3,4-dimethylphenyl)-1,4-cyclohexanediol

Following the procedure of Example 1 but substituting 3,4-dimethylphenylmagnesium bromide [prepared from 1-bromo-3,4-dimethylbenzene (obtained as in Ann. 419, 92) and magnesium], yields, cis and trans-1-(3,4-dimethylphenyl)-1,4-cyclohexanediol.

EXAMPLE 6 cis and trans 1-(2,4-dimethylphenyl)-1,4-cyclohexanediol

Following the procedure of Example 1 but substituting 2,4-dimethylphenylmagnesium bromide [prepared from 1-bromo-2,4-dimethylbenzene (obtained as in J. Amer. Chem. Soc. 38, 2545) and magnesium], yields cis and trans 1-(1,3-dimethylphenyl)-1,4-cyclohexanediol.

EXAMPLE 7 cis and trans 1-(2,5-dimethylphenyl)-1,4-cyclohexanediol

Following the procedure of Example 1 but substituting 2,5-dimethylphenylmagnesium bromide [prepared from 1-bromo-2,5-dimethylbenzene (obtained as in J. Amer. Chem. Soc. 38, 2545) and magnesium], yields cis and trans 1-(2,5-dimethylphenyl)-1,4-cyclohexanediol.

EXAMPLE 8 cis and trans 1-(p-ethylphenyl)-1,4-cyclohexanediol

Following the procedure of Example 1 but substituting (p-ethylphenyl)magnesium bromide [prepared from 1-bromo-4-ethylbenzene (obtained as in J. Amer. Chem. Soc. 38, 2545) and magnesium], yields cis and trans 1-(p-ethylphenyl)-1,4-cyclohexanediol.

EXAMPLE 9 cis and trans 1-(2,4-diethylphenyl)-1,4-cyclohexanediol

Following the procedure of Example 1 but substituting (2,4-diethylphenyl)magnesium bromide [prepared from 1-bromo-2,4-diethylbenzene (obtained as in J. Amer. Chem. Soc. 49, 3157) and magnesium], yields cis and trans 1-(2,4-diethylphenyl)-1,4-cyclohexanediol.

EXAMPLE 10 cis and trans 1-(o-trifluoromethylphenyl)-1,4-cyclohexanediol

Following the procedure of Example 1 but substituting 2-trifluoromethylphenylmagnesium bromide [prepared from (1-bromo-2-trifluoromethyl)benzene (obtained as in Chem. Ber. 93, 412) and magnesium], yields cis and trans 1-(o-trifluoromethylphenyl)-1,4-cyclohexanediol.

EXAMPLE 11 cis and trans 1-(p-isopropylphenyl)-1,4-cyclohexanediol

Following the procedure of Example 1 but substituting (4-isopropyl)phenylmagnesium bromide [prepared from (1-bromo-4-isopropyl)benzene (obtained as in Chem. Ber. 93, 412) and magnesium], yields cis and trans 1-(p-isopropyl-phenyl)-1,4-cyclohexanediol.

EXAMPLE 12

4-(p-fluorophenyl)-4-hydroxycyclohexanone

The cis and trans 1-(p-fluorophenyl)-1,4-cyclohexanediols obtained in Example 2 are dissolved together in acetone and cooled in an ice bath. Over the course of between about 5 and 10 minutes, 17 ml. of Jones reagent [chromium trioxide-sulfuric acid, prepared as in J. Chem. Soc. 39 (1946)] is added. The solvent is removed under vacuum and the residue dissolved in water and ether. The organic layer is washed with water and brine and taken to dryness. The residue is chromatographed over 500 ml. of Florisil. Elution is carried out with 2 l. of 5% acetone:Skellysolve B, 1 l. of 10% acetone:Skellysolve B and then 20% acetone:Skellysolve B to give 4-(p-fluorophenyl)-4-hydroxycyclohexanone, melting at 115° to 117° C.

Anal. Calcd. for $C_{12}H_{13}FO_2$: C, 69.21; H, 6.29. Found: C, 69.50; H, 6.76.

EXAMPLE 13

4-(p-methylphenyl)-4-hydroxycyclohexanone

Following the procedure of Example 12 but substituting cis and trans 1-(p-methylphenyl)-1,4-cyclohexanediol as starting material, yields 4-(p-methylphenyl)-4-hydroxycyclohexanone, which on recrystallization from cyclohexane has a melting point of 109° to 111° C.

Anal. Calcd. for $C_{13}H_{16}O_2$: C, 76.44; H, 7.90. Found: C, 77.04; H, 8.16.

EXAMPLE 14

4-(p-chlorophenyl)-4-hydroxycyclohexanone

Following the procedure of Example 12 but substituting cis and trans 1-(p-chlorophenyl)-1,4-cyclohexanediol as starting material, yields 4-(p-chlorophenyl)-4-hydroxycyclohexanone, which on recrystallization from acetone:cyclohexane has a melting point of 137.5° to 139° C.

Anal. Calcd for $C_{12}H_{13}ClO_2$: C, 64.14; H, 5.83. Found: C, 64.13; H, 6.02.

EXAMPLE 15

4-(p-trifluoromethylphenyl)-4-hydroxycyclohexanone

Following the procedure of Example 12 but substituting cis and trans 1-(p-trifluoromethylphenyl)-1,4-cyclohexanediol as starting material, yields 4-(p-trifluoromethylphenyl)-4-hydroxycyclohexanone, which on recrystallization from cyclohexane melts at 156° to 162° C.

Anal. Calcd. for $C_{13}H_{13}F_3O$: C, 60.63; H, 5.76. Found: C, 60.46; H, 5.07.

EXAMPLE 16

4-(2-chloro-6-methylphenyl-4-hydroxycyclohexanone

Following the procedure of Example 12 but substituting cis and trans 1-(2-chloro-6-methyl)phenyl-1,4-cyclohexanediol (obtained as in Example 3), yields 4-(2-chloro-6-methyl)phenyl-4-hydroxycyclohexanone.

EXAMPLE 17

4-(5-chloro-3-methyl)phenyl-4-hydroxycyclohexanone

Following the procedure of Example 12 but substituting cis and trans 1-(5-chloro-3-methyl)phenyl-1,4- cyclohexanediol (obtained as in Example 4), yields 4-(5-chloro-3-methyl)phenyl-4-hydroxycyclohexanone.

EXAMPLE 18

4-(3,4-dimethylphenyl)-4-hydroxycyclohexanone

Following the procedure of Example 12 but substituting cis and trans 1-(3,4-dimethylphenyl)-1,4-cyclohexanediol (obtained as in Example 5), yields 4-(3,4-dimethylphenyl)-4-hydroxycyclohexanone.

EXAMPLE 19

4-(2,4-dimethylphenyl)-4-hydroxycyclohexanone

Following the procedure of Example 12 but substituting cis and trans 1-(2,4-dimethylphenyl)-1,4-cyclohexanediol (obtained as in Example 6), yields 4-(2,4-dimethylphenyl)-4-hydroxycyclohexanone.

EXAMPLE 20

4-(2,5-dimethylphenyl)-4-hydroxycyclohexanone

Following the procedure of Example 12 but substituting cis and trans 1-(2,5-dimethylphenyl)-1,4-cyclohexanediol (obtained as in Example 7), yields 4-(2,5-dimethylphenyl)-4-hydroxycyclohexanone.

EXAMPLE 21

4-(p-ethylphenyl)-4-hydroxycyclohexanone

Following the procedure of Example 12 but substituting cis and trans 1-(p-ethylphenyl)-1,4-cyclohexanediol (obtained as in Example 8), yields 4-(p-ethylphenyl)-4-hydroxycyclohexanone.

EXAMPLE 22

4-(2,4-diethylphenyl)-4-hydroxycyclohexanone

Following the procedure of Example 12 but substituting cis and trans 1-(2,4-diethylphenyl)-1,4-cyclohexanediol (obtained as in Example 9), yields 4-(2,4-diethylphenyl)-4-hydroxycyclohexanone.

EXAMPLE 23

4-(o-trifluoromethylphenyl)-4-hydroxycyclohexanone

Following the procedure of Example 12 but substituting cis and trans 1-(o-trifluoromethylphenyl)-1,4-cyclohexanediol (obtained as in Example 10), yields 4-(o-trifluoromethylphenyl)-4-hydroxycyclohexanone.

EXAMPLE 24

4-(p-isopropylphenyl)-4-hydroxycyclohexanone

Following the procedure of Example 12 but substituting cis and trans 1-(p-isopropylphenyl)-1,4-cyclohexanediol (obtained in Example 11), yields 4-(p-isopropylphenyl)-4-hydroxycyclohexanone.

EXAMPLE 25

4-hydroxy-4-(p-fluorophenyl)cyclohexanone dimethyl ketal

To a solution of 9.38 g. (0.045 mole) of 4-(p-fluorophenyl)-4-hydroxycyclohexanone (prepared as in Example 12) in 100 ml. of methanol, 1 ml. of trifluoroacetic acid is added. Following standing at room temperature for about 2 hours, 10 g. of sodium bicarbonate is added. The solid material is removed by filtration and the filtrate evaporated to dryness. The residue is extracted with benzene and the extract evaporated to dryness. The solid obtained is recrystallized from Skellysolve B to give 10.23 g. (89% of theoretical yield) of 4-hydroxy-4-(p-fluorophenyl)-cyclohexanone dimethyl ketal, melting at 94° to 99° C. The analytical sample melts at 97° to 100° C.

Anal. Calcd. for $C_{14}H_{19}FO_3$: C, 66.12; H, 7.53. Found: C, 66.47; H, 7.83.

EXAMPLE 26

4-hydroxy-4-(p-methylphenyl)cyclohexanone dimethyl ketal

A solution of 9.81 g. (0.0048 mole) of 4-(p-methylphenyl)-4-hydroxycyclohexanone (prepared as in Example 13) and 2 ml. of trifluoroacetic acid in 200 ml. of methanol is allowed to stand at room temperature for about 5 hours. Ten grams of sodium bicarbonate is then added and the solid removed by filtration; the filtrate is evaporated to dryness. The resulting residue is thoroughly extracted with benzene and the extract evaporated to dryness. The solid obtained is recrystallized from Skellysolve B to give 10.62 g. (88%) of 4-hydroxy-4-(p-methylphenyl)cyclohexanone dimethyl ketal, melting at 96° to 100° C. The analytical sample melted at 93° to 97° C.

Anal. Calcd. for $C_{15}H_{22}O_3$: C, 71.97; H, 8.81. Found: C, 72.12; H, 9.25.

Following the procedure of Example 26 but substituting other starting materials, such as 1. 4-(m-chlorophenyl)-4-hydroxycyclohexanone,
2. 4-(2-chloro-6-methylphenyl)-4-hydroxycyclohexanone,
3. 4-(5-chloro-3-methylphenyl)-4-hydroxycyclohexanone,
4. 4-(3,4-dimethylphenyl)-4-hydroxycyclohexanone,
5. 4-(2,4-dimethylphenyl)-4-hydroxycyclohexanone,
6. 4-(2,5-dimethylphenyl)-4-hydroxycyclohexanone,
7. 4-(p-ethylphenyl)-4-hydroxycyclohexanone,
8. 4-(2,4-diethylphenyl)-4-hydroxycyclohexanone,
9. 4-(p-trifluoromethylphenyl)-4-hydroxycyclohexanone,
10. 4-(o-trifluoromethylphenyl)-4-hydroxycyclohexanone,
11. 4-(p-isopropylphenyl)-4-hydroxycyclohexanone, and the like, yields, respectively, 1. 4-(m-chlorophenyl)-4-hydroxycyclohexanone dimethyl ketal,
2. 4-(2-chloro-6-methylphenyl)-4-hydroxycyclohexanone dimethyl ketal,
3. 4-(5-chloro-3-methylphenyl)-4-hydroxycyclohexanone dimethyl ketal,
4. 4-(3,4-dimethylphenyl)-4-hydroxycyclohexanone dimethyl ketal,
5. 4-(2,4-dimethylphenyl)-4-hydroxycyclohexanone dimethyl ketal,
6. 4-(2,5-dimethylphenyl)-4-hydroxycyclohexanone dimethyl ketal,
7. 4-(p-ethylphenyl)-4-hydroxycyclohexanone dimethyl ketal,
8. 4-(2,4-diethylphenyl)-4-hydroxycyclohexanone dimethyl ketal,
9. 4-(p-trifluoromethylphenyl)-4-hydroxycyclohexanone dimethyl ketal,
10. 4-(o-trifluoromethylphenyl)-4-hydroxycyclohexanone dimethyl ketal,
11. 4-(p-isopropylphenyl)-4-hydroxycyclohexanone dimethyl ketal, and the like.

Following the procedure of the immediately preceding paragraph and of Example 26 but substituting other starting materials, such as 1. 4-(o-methylphenyl)-4-hydroxycyclohexanone,
2. 4-(m-methylphenyl)-4-hydroxycyclohexanone,
3. 4-(o-methoxyphenyl)-4-hydroxycyclohexanone,
4. 4-(p-chlorophenyl)-4-hydroxycyclohexanone,
5. 4-(m-trifluoromethylphenyl)-4-hydroxycyclohexanone, and the like, yields, respectively, 1. 4-(o-methylphenyl)-4-hydroxycyclohexanone dimethyl ketal, melting point 86° to 89° C. and Anal. Calcd. for $C_{15}H_{22}O_3$: C, 71.97; H, 8.86. Found: C, 72.29; H, 8.96.

2. 4-(m-methylphenyl)-4-hydroxycyclohexanone dimethyl ketal, m.p. 71° to 74° C. and Anal. Calcd. for $C_{15}H_{22}O_3$: C, 71.97; H, 8.86. Found: C, 72.27; H, 8.83.

3. 4-(o-methoxyphenyl)-4-hydroxycyclohexanone dimethyl ketal, m.p. 68° to 71° C. and Anal. Calcd. for $C_{15}H_{22}O_4$: C, 67.64; H, 8.33. Found: C, 67.74; H, 8.31.

4. 4-(p-chlorophenyl)-4-hydroxycyclohexanone dimethyl ketal, m.p. 91.5° to 97° C. and Anal. Calcd. for $C_{14}H_{19}ClO_3$: C, 62.10; H, 7.07; Cl, 13.10. Found: C, 62.48; H, 7.22; Cl, 13.05.

5. 4-(m-trifluoromethylphenyl)-4-hydroxycyclohexanone dimethyl ketal, and the like.

EXAMPLE 27

4-methoxy-4-(p-fluorophenyl)cyclohexaone

To a solution of 21.65 g. (0.085 mole) of 4-hydroxy-4-(p-fluorophenyl)cyclohexanone dimethyl ketal (prepared as in Example 25) in 80 ml. of dimethylformamide and 320 ml. of benzene, 3.56 g. of 57% sodium hydride is added. Following about 1 hour of stirring at room temperature, 35 ml. of methyl iodide is added and the mixture heated at reflux. After about 4 hours of heating an additional 10 ml. of methyl iodide is added. At the end of about 18 hours of heating, the suspension, after cooling, is washed with water and brine. The organic layer is evaporated to dryness and the gum remaining dissolved in 400 ml. of acetone, then 40 ml. of 2.5N hydrochloric acid added. At the end of about 4 hours, most of the solvent is removed under vacuum. The residue is extracted with ether and the organic layer washed with aqueous sodium bicarbonate solution and brine and then evaporated to dryness. The residual gum is chromatographed on a 2 l. column of Florisil (synthetic magnesium silicate), with elution by 2 l. of Skellysolve B, 2 l. of 95% Skellysolve B:5% acetone and 4 l. of 70% Skellysolve B:30% acetone. Crystalline fractions of first the product, then 6.87 g. (49%) of 4-hydroxy-4-(p-fluorophenyl)-cyclohexanone, melting at 108° to 114° C., are obtained. The product is recrystallized from petroleum ether to give 7.76 g. (41%) of 4-methoxy-4-(p-fluorophenyl)cyclohexanone, melting at 60° to 69° C. The analytical sample melts at 68° to 70° C.

Anal. Calcd. for $C_{13}H_{15}FO_2$: C, 70.25; H, 6.80. Found: C, 69.92; H, 6.77.

Following the procedure of Example 27 but substituting ethyl iodide, propyl iodide or butyl iodide for methyl iodide, yields, respectively, 4-ethoxy-4-(p-fluorophenyl)-cyclohexanone, 4-propoxy-4-(p-fluorophenyl)cyclohexanone or 4-butoxy-4-(p-fluorophenyl)cyclohexanone.

EXAMPLE 28

4-methoxy-4-(p-methylphenyl)cyclohexanone

To a solution of 13.10 g. (0.052 mole) of 4-hydroxy-4(p-methylphenyl)cyclohexanone dimethyl ketal (prepared as in Example 26) in 60 ml. of dimethylformamide and 180 ml. of benzene, 2.18 g. of sodium hydride is added. Following about 1 hour of stirring at room temperature and 1 hour at reflux, 20 ml. of methyl iodide is added and the mixture heated at reflux for about 8 hours. It is cooled and then washed with water and brine and the organic layer evaporated to dryness. The residue is dissolved in 250 ml. of methanol and 25 ml. of 2.5N hydrochloric acid added and the mixture stirred for about 2 hours at room temperature. Most of the solvent is removed under vacuum and the residue dissolved in ether. The organic layer is washed with aqueous sodium bicarbonate solution then brine and evaporated to dryness. The gum that remains is chromatographed on a 1.2 l. column of Florisil with elution by 1 l. of Skellysolve B, 6 l. of 95% Skellysolve B:5% acetone and 4 l. of 80% Skellysolve B:20% acetone. Crystalline fractions of first the product, then 3.48 g. (33%) of 4-hydroxy-4-(p-methylphenyl)-cyclohexanone. The product is recrystallized twice from petroleum ether to give 5.9 g. (52%) of 4-methoxy-4-(p-methylphenyl)cyclohexanone, melting at 76° to 76.5° C.

Anal. Calcd. for $C_{14}H_{18}O_2$: C, 77.03; H, 8.31. Found: C, 77.30; H, 8.72.

Following the procedure of Example 28 but substituting ethyl iodide, propyl iodide or butyl iodide for methyl iodide, yields, respectively, 4-ethoxy-4-(p-methylphenyl)-cyclohexanone, 4-propoxy-4-(p-methylphenyl)cyclohexanone or 4-butoxy-4-(p-methylphenyl)cyclohexanone.

Following the procedure of Example 28 but substituting other starting materials, such as 1. 4-(m-chlorophenyl)-4-hydroxycyclohexanone dimethyl ketal,
2. 4-(2-chloro-6-ethoxyphenyl)-4-hydroxycyclohexanone dimethyl ketal,
3. 4-(5-chloro-3-methylphenyl)-4-hydroxycyclohexanone dimethyl ketal,
4. 4-(3,4-dimethylphenyl)-4-hydroxycyclohexanone dimethyl ketal,
5. 4-(2,4-dimethylphenyl)-4-hydroxycyclohexanone dimethyl ketal,
6. 4-(2,5-dimethylphenyl)-4-hydroxycyclohexanone dimethyl ketal,
7. 4-(p-ethylphenyl)-4-hydroxycyclohexanone dimethyl ketal,
8. 4-(2,4-diethylphenyl)-4-hydroxycyclohexanone dimethyl ketal,
9. 4-(p-trifluoromethylphenyl)-4-hydroxycyclohexanone dimethyl ketal,
10. 4-(o-trifluoromethylphenyl)-4-hydroxycyclohexanone dimethyl ketal,
11. 4-(p-isopropylphenyl)-4-hydroxycyclohexanone dimethyl ketal, and the like, yields, respectively, 1. 4-methoxy-4-(m-chlorophenyl)cyclohexanone,
2. 4-methoxy-4-[(2-chloro-6-ethoxy)phenyl]-cyclohexanone,
3. 4-methoxy-4-[(5-chloro-3-methyl)phenyl]-cyclohexanone,
4. 4-methoxy-4-(3,4-dimethylphenyl)cyclohexanone,
5. 4-methoxy-4-(2,4-dimethylphenyl)cyclohexanone,
6. 4-methoxy-4-(2,5-dimethylphenyl)cyclohexanone,
7. 4-methoxy-4-(p-ethylphenyl)cyclohexanone,
8. 4-methoxy-4-(2,4-diethylphenyl)cyclohexanone,
9. 4-methoxy-4-(p-trifluoromethylphenyl)cyclohexanone, 10. 4-methoxy-4-(o-trifluoromethylphenyl)cyclohexanone, 11. 4-methoxy-4-(p-isopropylphenyl)cyclohexanone, and the like.

Following the procedure of Example 28 and the second paragraph thereafter but substituting other starting materials, such as 1. 4-(o-methylphenyl)-4-hydroxycyclohexanone dimethyl ketal,
2. 4-(m-methylphenyl)-4-hydroxycyclohexanone dimethyl ketal,
3. 4-(p-chlorophenyl)-4-hydroxycyclohexanone dimethyl ketal,
4. 4-(m-trifluoromethylphenyl)-4-hydroxycyclohexanone dimethyl ketal, and the like, yields, respectively, 1. 4-methoxy-4-(o-methylphenyl)cyclohexanone, melting point 73° to 75.5° C. and Anal. Calcd. for $C_{14}H_{18}O_2$: C, 77.03; H, 8.31. Found: C, 76.95; H, 8.39.

2. 4-methoxy-4-(m-methylphenyl)cyclohexanone, m.p. 42° to 45° C. and

Anal. Calcd. for $C_{14}H_{18}O_2$: C, 77.03; H, 8.31. Found: C, 77.08; H, 8.57.

3. 4-methoxy-4-(p-chlorophenyl)cyclohexanone, m.p. 55.5° to 59° C. and

Anal. Calcd. for $C_{13}H_{15}ClO_2$: C, 65.41; H, 6.33. Found: C, 65.64; H, 6.31.

4. 4-methoxy-4-(m-trifluoromethylphenyl)cyclohexanone, and the like.

Following the procedures of the three preceding paragraphs and of Example 28 but substituting other starting materials and alkyl iodides, such as 1. 4-(m-bromophenyl)-4-hydroxycyclohexanone dimethyl ketal and ethyl iodide,
2. 4-(2-fluoro-4-propylphenyl)-4-hydroxycyclohexanone dimethyl ketal and propyl iodide,
3. 4-(5-chloro-2-ethylphenyl)-4-hydroxycyclohexanone dimethyl ketal and butyl iodide,
4. 4-(2,4-dipropylphenyl)-4-hydroxycyclohexanone dimethyl ketal and ethyl iodide,
5. 4-(o-propylphenyl)-4-hydroxycyclohexanone dimethyl ketal and propyl iodide, and the like, yields, respectively, 1. 4-ethoxy-4-(m-bromophenyl)cyclohexanone,
2. 4-propoxy-4-[(2-fluoro-4-propyl)phenyl]cyclohexanone,
3. 4-butoxy-4-[(5-chloro-2-ethyl)phenyl]cyclohexanone,
4. 4-ethoxy-4-(2,4-dipropylphenyl)cyclohexanone, 120 ml. of ethanol is
5. 4-propoxy-4-(o-propylphenyl)cyclohexanone, and the like.

EXAMPLE 29

4-methoxy-4-(p-fluorophenyl)cyclohexanone oxime

A mixture of 5.85 g (0.027 mole) of 4-methoxy-4-(p-fluorophenyl)cyclohexanone (prepared as in Example 27), 6 g. of hydroxylamine hydrochloride and 12 ml. of aqueous 45% potassium hydroxide solution in 120 ml. of ethanol is heated at reflux for about 18 hours. The solvent is removed under vacuum and the residue dissolved in water and ether. The organic layer is washed with water and brine and evaporated to dryness. The solid remaining is recrystallized from Skellysolve B to give 5.28 g. (85%) of 4-methoxy-4-(p-fluorophenyl)cyclohexanone oxime, having a melting point of 86° to 89° C.

Anal. Calcd. for $C_{13}H_{16}FNO_2$: C, 65.80; H, 6.80. Found: C, 66.11; H, 6.78.

EXAMPLE 30

4-methoxy-4-(p-methylphenyl)cyclohexanone oxime

A mixture of 3.73 g. (0.17 mole) of 4-methoxy-4-(p-methylphenyl)cyclohexanone (prepared as in Example 28), 3.75 g. of hydroxylamine hydrochloride and 7.5 ml. of aqueous 50% potassium hydroxide solution in 70 ml. of ethanol is heated at reflux for about 4 hours. The solvent is removed under vacuum and the residue dissolved in water and ether. The organic layer is washed with water and brine and evaporated to dryness to give 4.04 g. (99%) of product. A sample recrystallized from aqueous methanol gives pure 4-methoxy-4-(p-methylphenyl)cyclohexanone oxime, having a melting point of 114° to 115.5° C.

Anal. Calcd. for $C_{14}H_{19}NO_2$: C, 72.07; H, 8.21; N, 6.00. Found: C, 72.08; H, 8.07; N, 5.89.

Following the procedure of Example 30 but substituting other starting materials, such as 1. 4-methoxy-4-(o-methylphenyl)cyclohexanone,
2. 4-methoxy-4-(m-methylphenyl)cyclohexanone,
3. 4-methoxy-4-(p-chlorophenyl)cyclohexanone,
4. 4-methoxy-4-(m-trifluoromethylphenyl)cyclohexanone, and the like, yields, respectively, 1. 4-methoxy-4-(o-methylphenyl)cyclohexanone oxime, melting point 108° to 110° C. and Anal. Calcd. for $C_{14}H_{19}NO_2$: C, 72.07; H, 8.21; N, 6.00. Found: C, 72.22; H, 8.21; N, 6.05.

2. 4-methoxy-4-(m-methylphenyl)cyclohexanone oxime, 3. 4-methoxy-4-(p-chlorophenyl)cyclohexanone oxime, m.p. 148° to 151° C. and Anal. Calcd. for $C_{13}H_{16}ClNO_2$: C, 61.53; H, 6.36; N, 5.52. Found: C, 61.55; H, 6.46; N, 5.32.

4. 4-methoxy-4-(m-trifluoromethylphenyl)cyclohexanone oxime, m.p. 98° to 100° C. and Anal. Calcd. for $C_{14}H_{16}F_3NO_2$: C, 58.53; H, 5.61; N, 4.88. Found: C, 58.43; H, 5.50; N, 4.83. and the like.

Following the procedure of Example 30 but substituting other starting materials, such as 1. 4-methoxy-4-(o-bromophenyl)cyclohexanone,
2. 4-ethoxy-4-[(2-chloro-4-fluoro)phenyl]cyclohexanone,
3. 4-propoxy-4-[(3-chloro-5-methyl)phenyl]cyclohexanone,
4. 4-isopropoxy-4-(m-ethylphenyl)cyclohexanone,
5. 4-butoxy-4-[(2-ethyl-6-methyl)phenyl]cyclohexanone,
6. 4-methoxy-4-(2,5-dibutylphenyl)cyclohexanone, and the like, yields, respectively, 1. 4-methoxy-4-(o-bromophenyl)cyclohexanone oxime,
2. 4-ethoxy-4-[(2-chloro-4-fluoro)phenyl]cyclohexanone oxime,
3. 4-propoxy-4-[(3-chloro-5-methyl)phenyl]cyclohexanone oxime,
4. 4-isopropoxy-4-(m-ethylphenyl)cyclohexanone oxime,
5. 4-butoxy-4-[(2-ethyl-6-methyl)phenyl]cyclohexanone oxime,
6. 4-methoxy-4-(2,5-dibutylphenyl)cyclohexanone oxime, and the like.

EXAMPLE 31

4-methoxy-4-(p-fluorophenyl)cyclohexanone oxime acetate

A mixture of 5.28 g. (0.23 mole) of 4-methoxy-4-(p-fluorophenyl)cyclohexanone oxime (prepared as in Example 29) and 20 ml. of acetic anhydride in 40 ml. of pyridine is allowed to stand at room temperature for about 18 hours. The mixture is then poured onto ice and water. The solid that separates is collected on a filter, dried and recrystallized from Skellysolve B to give 5.42 g. (85%) of pure 4-methoxy-4-(p-fluorophenyl)cyclohexanone oxime acetate, having a melting point of 87° to 88° C.

Anal. Calcd. $C_{15}H_{18}FNO_3$: C, 64.50; H, 6.49; N, 5.02. Found: C, 64.65; H, 6.67; N, 4.48.

Following the procedure of Example 31 but substituting propionic anhydride for acetic anhydride, yields 4-methoxy-4-(p-fluorophenyl)cyclohexanone oxime propionate.

EXAMPLE 32

4-methoxy-4-(p-methylphenyl)cyclohexanone oxime acetate

A mixture of 4.04 g. (0.017 mole) of 4-methoxy-4-(p-methylphenyl)cyclohexanone oxime (prepared as in Example 30) and 15 ml. of acetic anhydride in 30 ml. of pyridine is allowed to stand at room temperature for about 18 hours. The mixture is then poured into ice and water and the gum that precipitates is extracted with ether. The organic layer is washed successively with ice-cold 2.5N hydrochloric acid solution, water, aqueous sodium bicarbonate solution and brine. This solution is evaporated to dryness and the residue recrystallized from petroleum ether to give 4 g. (86%) of 4-methoxy-4-(p-methylphenyl)cyclohexanone oxime acetate, having a melting point of 68° to 70° C.

Anal. Calcd. for $C_{16}H_{21}NO_2$: C, 69.79; H, 7.69; N, 5.09. Found: C, 70.09; H, 7.39; N, 5.24.

Following the procedure of Example 32 but substituting propionic anhydride for acetic anhydride, yields 4-methoxy-4-(p-methylphenyl)cyclohexanone oxime propionate.

Following the procedure of Example 32 but substituting other starting materials, such as 1. 4-methoxy-4-(o-methylphenyl)cyclohexanone oxime,
2. 4-methoxy-4-(m-methylphenyl)cyclohexanone oxime,
3. 4-methoxy-4-(o-methoxyphenyl)cyclohexanone oxime,
4. 4-methoxy-4-(p-chlorophenyl)cyclohexanone oxime,
5. 4-methoxy-4-(m-trifluoromethylphenyl)cyclohexanone oxime, and the like, yields, respectively, 1. 4-methoxy-4-(o-methylphenyl)cyclohexanone oxime acetate, melting point 96° to 98.5° C. and Anal. Calcd. for $C_{16}H_{21}NO_3$: C, 69.79; H, 7.69; N, 5.09. Found: C, 69.14; H, 7.66; N, 5.23.

2. 4-methoxy-4-(m-methylphenyl)cyclohexanone oxime acetate,
3. 4-methoxy-4-(o-methoxyphenyl)cyclohexanone oxime acetate, m.p. 68° to 70° C. and Anal. Calcd. for $C_{16}H_{21}NO_4$: C, 65.95; H, 7.27; N, 4.81. Found: C, 65.81; H, 7.24; N, 4.75.

4. 4-methoxy-4-(p-chlorophenyl)cyclohexanone oxime acetate, m.p. 87° to 89.5° C. and Anal. Calcd. $C_{15}H_{18}ClNO_3$: C, 60.91; H, 6.13; N, 4.74. Found: C, 60.58; H, 6.14; N, 4.73.

5. 4-methoxy-4-(m-trifluoromethylphenyl)cyclohexanone oxime acetate, and the like.

Following the procedure of Example 32 but substituting other starting materials, such as 1. 4-methoxy-4-[(2-ethoxy-5-fluoro)phenyl]cyclohexanone oxime,
2. 4-ethoxy-4-(o-fluorophenyl)cyclohexanone oxime,
3. 4-butoxy-4-(2,5-difluorophenyl)cyclohexanone oxime,
4. 4-propoxy-4-(p-propylphenyl)cyclohexanone oxime, and the like, yields, respectively 1. 4-methoxy-4-[(2-ethoxy-5-fluoro)phenyl]cyclohexanone oxime acetate,
2. 4-ethoxy-4-(o-fluorophenyl)cyclohexanone oxime acetate,
3. 4-butoxy-4-(2,5-difluorophenyl)cyclohexanone oxime acetate,
4. 4-propoxy-4-(p-propylphenyl)cyclohexanone oxime acetate, and the like.

EXAMPLE 33

4-trans-(p-fluorophenyl)-4-cis-methoxycyclohexylamine hydrochloride (I)

To an ice cooled solution of 5.42 g. (0.0195 mole) of 4-methoxy-4-(p-fluorophenyl)cyclohexanone oxime acetate (prepared as in Example 31) in 25 ml. of tetrahydrofuran, 62 ml. of 1N diborane in tetrahydrofuran is cautiously added. After standing about 18 hours at room temperature, 1 ml. of water is cautiously added to the solution and the solvent removed under vacuum. The residue is then stirred for about 1 hour with 80 ml. of aqueous 0.5N hydrochloric acid and a small volume of ether. The organic layer is separated, washed with 20 ml. of water. The aqueous portions are combined, made strongly basic and extracted with ether, and the other extract washed with brine and evaporated to dryness. The residue is dissolved in ether and treated with 5 ml. of 4.9N hydrochloric acid in ether. The solid that precipitates is recrystallized, without heating, from methanol; ether to give 1.96 g. (49%) of 4-trans-(p-fluorophenyl)-4-cis-methoxycyclohexylamine hydrochloride (I), melting (with decomposition) at 264° to 266°C.

Anal. Calcd. for $C_{13}H_{19}ClFNO$: C, 60.11; H, 7.37; N, 5.39. Found: C, 59.67; H, 7.43; N, 5.22.

EXAMPLE 34

4-cis-methoxy-4-trans-(p-methylphenyl)-cyclohexylamine hydrochloride (I)

To an ice cooled solution of 4 g. (0.0156 mole) of 4-methoxy-4-(p-methylphenyl)cyclohexanone oxime acetate (prepared as in Example 31) in 20 ml. of tetrahydrofuran, 46 ml. of 1N diborane in tetrahydrofuran is cautiously added. After standing about 18 hours, 1 ml. of water is added dropwise to the mixture. After effervescence ceases, the solvent is removed under vacuum. The residue is then stirred for about 1 hour with 100 ml. of aqueous 0.5N hydrochloric acid and a small volume of ether. The organic layer is then separated and washed with 30 ml. of aqueous 0.5N hydrochloric acid and 30 ml. of water. The aqueous portions are combined, made strongly basic and extracted with ether, and the ether extract washed with brine and evaporated to dryness. The residue is dissolved in ether and the solution treated with 2 ml. of 4.9N hydrochloric acid in ether. The solid that precipitates is dissolved in methanol and slowly reprecipitated with ether to give 1.88 g (49%) of 4-cis-methoxy-4-trans-(p-methylphenyl)cyclohexylamine hydrochloride (I), melting above 300°C.

Anal. Calcd. for $C_{14}H_{22}ClNO$: C, 65.73; H, 8.67; N, 5.98. Found: C, 65.88; H, 8.30; N, 5.39.

Following the procedure of Example 34 but substituting for hydrochloric acid another acid such as hydrobromic, sulfuric, phosphoric, nitric, benzoic, naphthoic, salicylic, tartaric, nicotinic, cyclohexanesulfamic, hexynoic, lactic, palmitic, glutaric, acetic, propionic, phenylbutyric acid, and the like, yields a corresponding acid addition salt of a 4-cis-alkoxy-4-trans-(substituted phenyl)cyclohexylamine (I).

Following the procedure of Example 34 but substituting other starting materials, such as 1. 4-methoxy-4-(o-methylphenyl)cyclohexanone oxime acetate,
2. 4-methoxy-4-(m-methylphenyl)cyclohexanone oxime acetate,
3. 4-methoxy-4-(o-methoxyphenyl)cyclohexanone oxime acetate,
4. 4-methoxy-4-(p-chlorophenyl)cyclohexanone oxime acetate,
5. 4-methoxy-4-(m-trifluoromethylphenyl)cyclohexanone oxime acetate, and the like, yields, respectively, 1. 4-cis-methoxy-4-trans-(o-methylphenyl)cyclohexylamine hydrochloride (I), melting point 230° to 232°C. and Anal. Calcd. for $C_{14}H_{22}ClNO$: C, 65.73, H, 8.67; N, 5.48. Found: C, 65.48; H, 8.81; N, 5.50.

2. 4-cis-methoxy-4-trans-(m-methylphenyl)cyclohexylamine hydrochloride (I), m.p. 176° to 178° C. and Anal. Calcd. for $C_{14}H_{22}ClNO.1/2H_2O$: C, 64.62; H, 8.81; N, 5.26. Found: C, 64.73; H, 8.70; N, 5.34.

3. 4-cis-methoxy-4-trans-(o-methoxyphenyl)cyclohexylamine hydrochloride (I), m.p. 191° to 193° C. and Anal. Calcd. for $C_{14}H_{22}ClNO_2.H_2O$: C, 58.01; H, 8.35; N, 4.87. Found: C, 57.57; H, 8.13; N, 5.73.

4. 4-trans-(p-chlorophenyl)-4-cis-methoxycyclohexylamine hydrochloride (I), m.p. 256° to 258°C. and Anal. Calcd. for $C_{13}H_{19}ClNO$: C, 56.53; H, 6.93; N, 5.07. Found: C, 56.83; H, 6.88; N, 5.11.

5. 4-cis-methoxy-4-trans-(m-trifluoromethylphenyl)cyclohexylamine hydrochloride (I), m.p. 202° to 203° C. and Anal. Calcd. for $C_{14}H_{19}ClF_3NO$: C, 54.28; H, 6.18; N, 4.52. Found: C, 54.20; H, 5.83; N, 4.88. and the like.

Following the procedure of Example 34 but substituting other starting materials, such as 1. 4-ethoxy-4-[(2-ethoxy-6-fluoro)phenyl]cyclohexanone oxime acetate,
2. 4-propoxy-4-(p-trifluoromethylphenyl)cyclohexanone oxime propionate,
3. 4-ethoxy-4-[(2-ethyl-5-fluoro)phenyl]cyclohexanone oxime acetate,
4. 4-methoxy-4-[(5-methyl-2-propoxy)phenyl]cyclohexnone oxime acetate,
5. 4-ethoxy-4-[(2-fluoro-5-methyl)phenyl]cyclohexanone oxime acetate,
6. 4-propoxy-4-(o-propylphenyl)cyclohexanone oxime propionate,
7. 4-butoxy-4-(2,5-dimethylphenyl)cyclohexanone oxime acetate,
8. 4-butoxy-4-(2,4-diethylphenyl)cyclohexanone oxime acetate,
9. 4-butoxy-4-[(2-chloro-6-fluoro)phenyl]cyclohexanone oxime acetate,
10. 4-ethoxy-4-[(2-ethyl-5-methoxy)phenyl]cyclohexanone oxime acetate, and the like. yields, respectively, 1. 4-cis-ethoxy-4-trans-[(2-ethoxy-6-fluoro)phenyl]-cyclohexylamine hydrochloride (I),
2. 4-cis-propoxy-4-trans-(p-trifluoromethylphenyl)-cyclohexylamine hydrochloride (I),
3. 4-cis-ethoxy-4-trans-[(2-ethyl-5-fluoro)phenyl]-cyclohexylamine hydrochloride (I),
4. 4-cis-methoxy-4-trans-[(5-methyl-2-propoxy)-phenyl]cyclohexylamine hydrochloride (I),
5. 4-cis-ethoxy-4-trans-[(2-fluoro-5-methyl)phenyl]-cyclohexylamine hydrochloride (I),
6. 4-cis-propoxy-4-trans-(o-propylphenyl)cyclohexylamine hydrochloride (I),
7. 4-cis-butoxy-4-trans-(2,5-dimethylphenyl)-cyclohexylamine hydrochloride (I),
8. 4-cis-butoxy-4-trans-(2,4-dimethylphenyl)-cyclohexylamine hydrochloride (I),
9. 4-cis-butoxy-4-trans-[(2-chloro-6-fluoro)phenyl]-cyclohexylamine hydrochloride (I),
10. 4-cis-ethoxy-4-trans-[(2-ethyl-5-methoxy)-phenyl]-cyclohexylamine hydrochloride (I), and the like,

EXAMPLE 35

1-[4-trans-(p-fluorophenyl)-4-cis-methoxycyclohexyl]piperidine hydrochloride (I)

To a solution of 2 g. of 4-trans-(p-fluorophenyl)-4-cis-methoxycyclohexylamine hydrochloride (I) (prepared as in Example 33) in 35 ml. of ethanol, 2.5 ml. of 4.18N sodium methoxide in methanol is added. The mixture is stirred for about 1 hour and 3 g. of 1,5-diiodopentane and 2.5 g. of potassium carbonate is then added. The mixture is then heated at reflux for about 16 hours. Most of the solvent is removed under vacuum and the residue dissolved in ether and water. The organic layer is washed with water and brine and evaporated to dryness. The residue is dissolved in ether and treated with 3.6N ethereal hydrogen chloride. The precipitated solid is recrystallized twice from methanol:ethyl acetate to yield pure 1-[4-trans-(p-fluorophenyl)-4-cis-methoxycyclohexyl]piperidine hydrochloride (I).

Following the procedure of Example 35 but substituting ethereal p-toluenesulfonic acid for ethereal hydrogen chloride, yields 1-[4-trans-(p-fluorophenyl)-4-cis-methoxycyclohexyl]piperidine p-toluenesulfonate (I).

EXAMPLE 36

1-[4-cis-methoxy-4-trans-(p-methylphenyl)-cyclohexyl]piperidine hydrochloride (I)

To a solution of 2 g. of 4-cis-methoxy-4-trans-(p-methylphenyl)cyclohexylamine hydrochloride (I) (prepared as in Example 34) in 35 ml. of ethanol, 2.5 ml. of 4.18N sodium methoxide in methanol is added. The mixture is stirred for about 1 hour and 3 g. of 1,5-diiodopentane and 2.5 g. of potassium carbonate is then added. The mixture is then heated at reflux for about 16 hours. Most of the solvent is removed under vacuum and the residue dissolved in ether and water. The organic layer is washed with water and brine and evaporated to dryness. The residue is dissolved in ether and treated with 3.6N ethereal hydrogen chloride. The precipitated solid is recrystallized twice from methanol:ethyl acetate to yield pure 1-[4-cis-methoxy-4-trans-(p-methylphenyl)cyclohexyl]piperidine hydrochloride (I).

Following the procedure of Example 36 but substituting ethereal hydrogen chloride, yields 1-[4-cis-methoxy-4-trans-(p-methylphenyl)cyclohexyl]piperidine p-toluenesulfonate (I).

Following the procedure of Example 36 but substituting other starting materials, such as 1. 4-cis-ethoxy-4-trans-[(2-ethyl-6-fluoro)phenyl]-cyclohexylamine hydrochloride (I),
2. 4-cis-methoxy-4-trans-(p-trifluoromethylphenyl)-cyclohexylamine hydrochloride (I),
3. 4-cis-propoxy-4-trans-[(5-propyl-2-propoxy)-phenyl]cyclohexylamine hydrochloride (I),
4. 4-cis-butoxy-4-trans-[(5-ethyl-2-methyl)phenyl]-cyclohexylamine hydrochloride (I),
5. 4-cis-butoxy-4-trans-(2,5-dichlorophenyl)-cyclohexylamine hydrochloride (I), and the like, yields, respectively, 1. 1-{4-cis-ethoxy-4-trans-[2-ethyl-6-fluoro)phenyl]-cyclohexyl} piperidine hydrochloride (I),
2. 1-[4-cis-methoxy-4-trans-(p-trifluoromethylphenyl)-cyclohexyl]piperidine hydrochloride (I),
3. 1-{4-cis-propoxy-4-trans-[(5-propyl-2-propoxy)-phenyl]cyclohexy} piperidine hydrochloride (I),
4. 1-{4-cis-butoxy-4-trans-[5-ethyl-2-methyl)-phenyl]-cyclohexyl} piperidine hydrochloride (I),
5. 1-[4 lcis-butoxy-4-trans-(2,5-dichlorophenyl)-cyclohexyl] piperidine hydrochloride (1), and the like.

EXAMPLE 37

1-[4-trans-9-fluorophenyl)-4-cis-methoxy-cyclohexyl] pyrrolidine hydrochloride (I)

To a suspension of 2 g. of 4-trans-(p-fluorophenyl)-4-cis-methoxycyclohexylamine hydrochloride (I) (prepared as in Example 33) in 35 ml. of ethanol, 2.2 ml of 4.18N sodium methoxide in methanol is added. Following about 1 hour of stirring 2 g. of 1,4-dibromobutane and 2.5 g. of potassium carbonate is then added. The mixture is then heated at reflux for abut 16 hours and then evaporated to dryness and the residue dissolved in ether and water. The organic layer is washed with water and brine and evaporated to dryness. The residue is dissolved in ether and treated with 3.6N ethereal hydrogen chloride. The precipitated solid is recrystallized twice from methanol:ethyl acetate to give pure 1-[4-trans-(p-fluorophenyl)-4-cis-methoxy-cyclohexyl]pyrrolidine hydrochloride (I).

EXAMPLE 38

1-[4-cis-methoxy-4-trans-(p-methylphenyl)-cyclohexyl]pyrrolidine hydrochloride (I)

Following the procedure of Example 37 but substituting 4-cis-methoxy-4-trans-(p-methylphenyl)cyclohexylamine hydrochloride (I) (prepared as in Example 34) as starting material, yields 1-[4-cis-methoxy-4-trans-(p-methylphenyl)-cyclohexyl]pyrrolidine hydrochloride (I).

Following the procedure of Example 38 but substituting other starting materials, such as 1. 4-cis-ethoxy-4-trans-[2-fluoro-5-methyl)phenyl]-cyclohexylamine hydrochloride (I),
2. 4-cis-methoxy-4-trans-[(5-methyl-2-propyl)-phenyl]-cyclohexylamine hydrochloride (I),
3. 4-cis-propoxy-4-trans-(m-trifluoromethylphenyl)-cyclohexylamine hydrochloride (I),
4. 4-cis-butoxy-4-trans-[(3-chloro-5-methoxy)-phenyl]-cyclohexylamine hydrochloride (I),
5. 4-cis-butoxy-4-trans-(2,4-dimethylphenyl)cyclohexylamine hydrochloride (I), and the like, yields, respectively, 1. 1-{4-cis-ethoxy-4-trans-[(2-fluoro-5-methyl)-phenyl]-cyclohexyl} pyrrolidine hydrochloride (I),
2. 1-{4-cis-methoxy-4-trans-[(5-methyl-2-propyl)-phenyl]cyclohexyl} pyrrolidine hydrochloride (I),
3. 1-[4-cis-propoxy-4-trans-(m-trifluoromethylphenyl)-cyclohexyl]pyrrolidine hydrochloride (I),
4. 1-{4-cis-butoxy-4-trans-[(3-chloro-5-methoxy)-phenyl]cyclohexyl} pyrrolidine hydrochloride (I),
5. 1-[4-cis-butoxy-4-trans-(2,4-dimethylphenyl)-cyclohexyl]pyrroldine hydrochloride (I), and the like.

EXAMPLE 39

1-[4-trans-(p-fluorophenyl)-4-cis-methoxycyclohexyl]hexamethyleneimine hydrochloride (I)

Following the procedure of Example 35 but substituting 1,6-diiodohexane for 1,5-diiodopentane yields 1-[4-trans-(p-fluorophenyl)-4-cis-methoxycyclohexyl]-hexamethyleneimine hydrochloride (I).

EXAMPLE 40

1-[4-cis-methoxy-4-trans-(p-methylphenyl)-cyclohexyl]hexamethyleneimine hydrochloride (I)

Following the procedure of Example 36 but substituting 1,6-diiodohexane for 1,5-diiodopentane yields 1-[4-cis-methoxy-4-trans-(p-methylphenyl)cyclohexyl]-hexamethyleneimine hydrochloride (I).

Similarly, employing other dihaloalkanes with appropriate modifications of the procedures described in Examples 35 through 40, yields representative 1-[4-cis-alkoxy-4-trans-(substituted phenyl)cyclohexyl]single ring unsubstituted and monosubstituted heterocyclic compounds (e.g., piperidines, pyrrolidines, hexamethyleneimines, morpholines and piperazines), such as 1-[4-cis-methoxy-4-trans-(o-methylphenyl)cyclohexyl]-3-propylpyrrolidine hydrochloride (I), 1-[4-cis-butoxy-4-trans-(m-chlorophenyl)cyclohexyl]-3-ethylpiperidine hydrochloride (I), 11-{4-cis-butoxy-4-trans-[(2-fluoro-5-methoxy)phenyl]cyclohexyl}-3-methoxyhexamethyleneimine hydrochloride (I), 1-[4-cis-propoxy-4-trans-(p-trifluoromethylphenyl)cyclohexyl]morpholine hydrochloride (I), 1-{4-cis-ethoxy-4-trans-[(5-fluoro-2-ethyl)phenyl]-cyclohexyl}-2-methylmorpholine hydrochloride (I), 1--{-cis-propoxy-4-trans-[2,4,6-tripropyl)phenyl]cyclohexyl}piperazine hydrochloride (I), and the like.

EXAMPLE 41

4'-fluoro-4-{[4-trans-(p-fluorophenyl)-4-cis-methoxycyclohexyl]amino}butyrophenone hydrochloride (I)

To a solution of 1.96 g. (7.5 mmoles) of 4-trans-(p-fluorophenyl)-4-cis-methoxycyclohexylamine hydrochloride (I) (prepared as in Example 33) in 35 ml. of dimethylformamide, 0.32 g. of 57% sodium hydride is added. Following about 1 hour of stirring, 1.29 g. of potassium iodide and 2.15 g. of potassium carbonate and 1.92 g. of the 2,2-dimethyl-1,3-propanediol ketal of 4-chloro-4'-fluorobutyrophenone are added. The mixture is stirred at about 90° C. for about 17 hours and the solvent then removed under vacuum. The residue is dissolved in water and benzene. The organic layer is washed with water and brine and then evaporated to dryness. To a solution of the residue dissolved in 30 ml. of methanol, 15 ml. of 2.5N hydrochloric acid solution is added. Following about 1 hour of stirring most of the methanol is removed under vacuum and the solid collected on a filter, recrystallized from methanol:ether (without heating) to give 1.18 g. (34%) of 4'-fluoro-4-{[4-trans-(p-fluorophenyl)-4-cis-methoxycyclohexyl]amino}-butyrophenone hydrochloride (I), having a melting point of 176° to 178° C.

Anal. Calcd. for $C_{23}H_{28}ClF_2NO_2$: C, 65.16; H, 6.66; N, 3.30. Found: C, 64.87; H, 6.59; N, 3.18.

EXAMPLE 42

4'-fluoro-4-{[4-cis-methoxy-4-trans-(p-methylphenyl)-cyclohexyl]amino}butyrophenone hydrochloride (I)

To a solution of 1.88 g. (7.3 mmole) of 4-cis-methoxy-4-trans-(p-methylphenyl)cyclohexylamine hydrochloride (I) (prepared as in Example 34) in 35 ml. of dimethylformamide, 0.31 g. of 57% sodium hydride is added. Following about 1 hour of stirring, 1.24 g. of potassium iodide, 2.08 g. of potassium carbonate and 1.85 g. of the 2,2-dimethyl-1,3-propanediol ketal of 4-chloro-4'-fluorobutyrophenone are added. The mixture is stirred at about 90° C. for about 17 hours and the solvent then removed under vacuum. The residue is dissolved in water and benzene. The organic layer is washed with water and brine and then evaporated to dryness. To a solution of the residue dissolved in 20 ml. of methanol, 10 ml. of 2.5N hydrochloric acid solution is added. Following about 1 hour of stirring most of the methanol is removed under vacuum and the solid collected on a filter, recrystallized methylene chloride-ethyl (without heating) to give 0.78 g. (26%) of 4'-fluoro-4-{[4-cis-methoxy-4-trans-(p-methylphenyl)cyclohexyl]amino}butyrophenone hydrochloride (I), melting at 170° to 174° C. (with decomposition).

Anal. Calcd. for $C_{24}H_{31}ClFNO_2$: C, 68.64; H, 7.44; N, 3.34. Found: C, 67.63; H, 7.50; N, 3.42.

Following the procedure of Example 42 but substituting other starting materials, such as 1. 4-cis-methoxy-4-trans-(o-methylphenyl)cyclohexylamine hydrochloride (I),
2. 4-cis-methoxy-4-trans-(m-methylphenyl)cyclohexylamine hydrochloride (I),
3. 4-cis-methoxy-4-trans-(o-methoxyphenyl)cyclohexylamine hydrochloride (I),
4. 4-trans-(p-chlorophenyl)-4-cis-methoxycyclohexylamine hydrochloride (I),
5. 4-cis-methoxy-4-trans-(m-trifluoromethylphenyl)cyclohexylamine hydrochloride (I), and the like, yields, respectively, 1. 4'-fluoro-4-{[4-cis-methoxy-4-trans-(o-methylphenyl)cyclohexyl]amino}butyrophenone hydrochloride (I), melting point 163° to 166° C. and
Anal. Calcd. for $C_{24}H_{31}ClFNO_2 \cdot 1/2H_2O$: C, 67.19; H, 7.52; N, 3.27. Found: C, 67.26; H, 7.40; N, 3.37;
2. 4'-fluoro-4-{[4-cis-methoxy-4-trans-(m-methlphenyl)cyclohexyl]amino}butyrophenone hydrochloride (I), m.p. 167° to 170° C. and
Anal. Calcd. for $C_{24}H_{31}ClFNO_2$: C, 68.64; H, 7.44; N, 3.34. Found: C, 68,08; H, 7.39; N, 3.23.
3. 4'-fluoro-4-{[4-cis-methoxy-4-trans-(o-methoxyphenyl)cyclohexyl]amino}butyrophenone hydrochloride (I),
Anal. Calcd. for $C_{24}H_{31}ClFNO_3$: C, 65.12; H, 7.17; N, 3.21. Found: C, 67.42; H, 7.33; N, 3.61.
4. 4'-fluoro-4-{[4-trans-(p-chlorophenyl)-4-cis-methoxycyclohexyl]amino}butyrophenone hydrochloride (I), m.p. 185° to 188° C. and
Anal. Calcd. for $C_{24}H_{31}ClFNO_3$: C, 62.73; H, 6.41; N, 3.18. Found: C, 62.19; H, 6.34; N, 3.17.
5. 4'-fluoro-4-{[4-cis-methoxy-4-trans-(m-trifluoromethylphenylcyclohexyl]amino}butyrophenone hydrochloride (I), m.p. 189° to 191° C. and
Anal. Calcd. for $C_{24}H_{28}ClF_4NO_2$: Cl, 60.82; H, 5.95; N, 2.96. Found: C, 60.58; H, 4.97; N, 2.88.
and the like.

Following the procedure of Example 42 but substituting the acid addition salt of another 4-cis-alkoxy-4-trans-(substituted phenyl)cyclohexylamine (I) as starting material and the 2,2-dimethyl-1,3-propanediol ketal of another ω-haloalkanaryl ketone, such as 1. 4-cis-ethoxy-4-trans-[(3-ethyl-5-fluoro)phenyl]cyclohexylamine hydrochloride (I) and the 2,2-dimethyl-1,3-propanediol ketal of 4'-bromo-4-chlorobutyrophenone,
2. 4-cis-methoxy-4-trans-(2,6-diethylphenyl)cyclohexylamine hydrobromide (I) and the 2,2-dimethyl-1,3-propanediol ketal of 4-chloro-4'-ethoxybutyrophenone,
3. 4-cis-butoxy-4-trans-[(2-chloro-6-fluoro)phenyl]cyclohexylamine hydrochloride (I) and the 2,2-dimethyl-1,3-propanediol ketal of 3',4-dichlorobutyrophenone,
4. 4-cis-butoxy-4-trans-[(3-ethoxy-5-fluoro)phenyl]cyclohexylamine hydrochloride (I) and the 2,2-dimethyl-1,3-propanediol ketal of 3-chloro-4'-methylpropiophenone,
5. 4-cis-propoxy-4-trans-[2-propoxy-6-propyl)phenyl]-cyclohexylamine cyclohexanesulfamate (I) and the 2,2-dimethyl-1,3-propanediol ketal of 5-chloro-4'-ethylvalerophenone, and the like, yields, respectively, 1. 4'-bromo-4-{[4-cis-ethoxy-4-trans-(3-ethyl-5-fluorophenyl)cyclohexyl]amino}butyrophenone hydrochloride (I),
2. 4'-ethoxy-4-[4-cis-methoxy-4-trans-(2,6-diethylphenyl)cyclohexyl]amino butyrophenone hydrobromide (I),
3. 3'-chloro-4-{[4-cis-butoxy-4-trans-(2-chloro-6-fluorophenyl)cyclohexyl]amino}butyrophenone hydrochloride (I),
4. 4'-methyl-3-{[4-cis-butoxy-4-trans-(3-ethoxy-5-fluorophenyl)cyclohexyl]amino}propiophenone hydrochloride (I),
5. 4'-ethyl-5-{[4-cis-propoxy-4-trans-(2-propoxy-6-propylphenyl)cyclohexyl]amino}valerophenone cyclohexanesulfamate (I), and the like.

EXAMPLE 43

4'-fluoro-4-{[4-trans-(p-fluorophenyl)-4-cis-methoxycyclohexyl]methylamino}butyrophenone hydrochloride (I)

a. N-[4-trans-(p-fluorophenyl)-4-cis-methoxycyclohexyl]formamide (I)

A mixture of 2.5 g. of the free base form of 4-trans-(p-fluorophenyl)-4-cis-methoxycyclohexylamine hydrochloride (I) [obtained by stirring 3 g. of an ether solution of its hydrochloride (prepared as in Example 33) with 2.5 ml. of triethylamine] and 30 ml. of ethyl formate is heated at reflux for about 40 hours. The resulting solution is evaporated to dryness and the residue recrystallized from benzene to give N-[4-trans-(p-fluorophenyl)-4-cis-methoxycyclohexyl]formamide (I).

Following the procedure of (a), above, but substituting other esters for ethyl formate, such as ethyl acetate, methyl propionate, ethyl butyrate and the like, yields, respectively N-[4-trans-(p-fluorophenyl)-4-cis-methoxycyclohexyl]acetamide (I), N-[4-trans-(p-fluorophenyl)-4-cis-methoxycyclohexyl]propionamide (I), N-[4-trans-(p-fluorophenyl)-4-cis-methoxycyclohexyl]butyramide (I), and the like.

b. N-methyl-[4-trans-(p-fluorophenyl)-4-cis-methoxycyclohexyl]amine hydrochloride (I)

A solution of 2.5 g. of 4-trans-N-[4-(p-fluorophenyl)-4-cis-methoxycyclohexyl]formamide (I) [obtained as in (a), above] in 75 ml. of tetrahydrofuran is added to a well stirred suspension of 0.65 g. of lithium aluminum hydride in 15 ml. of tetrahydrofuran. After heating this mixture at reflux for about 4 hours it is cooled in ice, and 0.6 ml. of water, 0.6 ml. of 15% aqueous sodium hydroxide solution and 1.7 ml. of water are added successively. The solid that precipitates is removed by filtration and the filtrate evaporated to dryness. The residue is dissolved in ether and treated with a small excess of 3.6N ethereal hydrogen chloride. The solid that precipitates is recrystallized from methylene chloride:ethyl acetate to give N-methyl-[4-trans-(p-fluorophenyl)-4-cis-methoxycyclohexyl]amine hydrochloride (I).

Following the procedure of (b), above, but substituting N-[4-trans-(p-fluorophenyl)-4-cis-methoxycyclohexyl]-acetamide (I), N-[4-trans-(p-fluorophenyl)-4-cis-methoxy-cyclohexyl]propionamide (I), N-[4-trans-(p-fluorophenyl)-4-cis-methoxycyclohexyl]-butyramide (I), and the like, as starting materials, yields, respectively, N-ethyl-[4-trans-(p-fluorophenyl)-4-cis-methoxycyclohexyl]amine hydrochloride (I), N-propyl-[4-trans-(p-fluorophenyl)-4-cis-methoxycyclohexyl]amine hydrochloride (I), N-butyl-[4-trans-(p-fluorophenyl)-4-cis-methoxycyclohexyl]amine hydrochloride (I), and the like.

c. 4'-fluoro-4-{[4-trans-(p-fluorophenyl)-4-cis-methoxycyclohexyl]methylamino}butyrophenone hydrochloride (I)

To a suspension of 2 g. of N-methyl-[4-trans-(p-fluoro-phenyl)-4-cis-methoxycyclohexyl]amine hydrochoride (I) [prepared as in (b), above] in 30 ml. of dimethylformamide, 0.4 g. of sodium hydride (56% in mineral oil) is added. Following about 30 minutes of stirring there is added successively, 2.6 g. of potassium carbonate, 1,6 g. of potassium iodide and 2.5 g. of the 2,2-dimethyl-1,3-propanediol ketal of 4-chloro-4'-fluorobutyrophenone. The mixture is stirred at about 90° C. for about 18 hours, allowed to cool and diluted with benzene and water. The organic layer is washed with water and brine and evaporated to dryness. A solution of the residue in 70 ml. of methanol and 35 ml. of 2.5N hydrochloric acid is stirred for about 2 hours at room temperature. The methanol is then removed under vacuum and the residue extracted with methylene chloride. The organic layer is washed once with 2.5N hydrochloric acid and evaporated to dryness. The residual solid is recrystallized twice from methylene chloride:ethyl acetate to give 4'-fluoro-4-{[4-trans-(p-fluorophenyl)-4-cis-methoxycyclohexyl]-methylamino}butyrophenone hydrochloride (I).

Following the procedure of (c), above, but substituting N-ethyl[4-trans-(p-fluorophenyl)-4-cis-methoxycyclohexyl]-amine hydrochloride (I), N-propyl-[4-trans-(p-fluorophenyl)-4-cis-methoxycyclohexyl]amine hydrochloride (I), N-butyl-[4-trans-(p-fluorophenyl)-4-cis-methoxycyclohexyl]amine hydrochloride (I), and the like, yields, respectively, 4'-fluoro-4-{[4-trans-(p-fluorophenyl)-4-cis-methoxycyclohexyl]-ethylamino}butyrophenone hydrochloride (I), 4'-fluoro-4-{[4-trans-(p-fluorophenyl)-4-cis-methoxycyclohexyl]propylamino}butyrophenone hydrochloride (I), 4'-fluoro-4-{[4-trans-(p-fluorophenyl)-4-cis-methoxycyclohexyl]butylamino}-butyrophenone hydrochloride (I), and the like.

EXAMPLE 44

4'-fluoro-4-{[4-cis-methoxy-4-trans-(p-methylphenyl)-cyclohexyl]methylamino}butyrophenone hydrochloride (I)

Following the procedure of Example 43 but substituting the free base form of 4-cis-methoxy-4-trans-(p-methylphenyl)-cyclohexylamine hydrochloride (I) (prepared as in Example 34) as starting material, yields, respectively, (a) N-[4-cis-methoxy-4-trans-(p-methylphenyl)cyclohexyl]formamide (I), (b) N-methyl-[4-cis-methoxy-4-trans-(p-methylphenyl)-cyclohexyl]amine hydrochloride (I) and (c) 4'-fluoro-4-{[4-cis-methoxy-4-trans-(p-methylphenyl)cyclohexyl]methylamino}-butyrophenone hydrochloride (I).

Following the procedure of Examples 43 and 44 but substituting other starting materials and other esters for ethyl formate in (a) of the former example, such as 1. 4-cis-ethoxy-4-trans-[3-ethyl-6-fluoro)phenyl]-cyclohexylamine hydrochloride (I) and ethyl acetate,
2. 4-cis-methoxy-4-trans-[(3-propoxy-5-propyl)-phenyl]-cyclohexylamine hydrochloride (I) and methyl propionate,
3. 4-cis-propoxy-4-trans-(p-trifluoromethylphenyl)-cyclohexylamine hydrochloride (I) and ethyl butyrate,
4. 4-cis-butoxy-4-trans-(1,4-diethylphenyl)cyclohexylamine hydrochloride (I) and methyl acetate,
5. 4-cis-butoxy-4-trans-[3-chloro-5-fluoro)phenyl]-cyclohexylamine hydrochloride (I) and ethyl propionate, and the like, yields, respectively, 1 a. N-{[4-cis-ethoxy-4-trans-(5-ethyl-2-fluoro)-phenyl]cyclohexyl}acetamide (I), b. N-ethyl-{[4-cis-ethoxy-4-trans-(3-ethyl-4-trans-(3-ethyl-6-fluoro)phenyl]cyclohexyl}amine hydrochloride (I), c. 4'-fluoro-4-{[4-cis-ethoxy-4-trans-(5-ethyl-2-fluorophenyl)cyclohexyl]ethylamino}butyrophenone hydrochloride (I), 2. a. N-{[4-cis-methoxy-4-trans-(3-propoxy-5-propylphenyl]cyclohexyl}propionamide (I), b. N-propyl-{[4-cis-methoxy-4-trans-(3-propoxy-5-propyl)phenyl]cyclohexyl}amine hydrochloride (I), c. 4'-fluoro-4-{[4-cis-methoxy-4-trans-(3-propoxy-5-propylphenyl)cyclohexyl]-propylamino}butyrophenone hydrochloride (I), 3. a. N-[4-cis-propoxy-5-trans-(p-trifluoromethylphenyl)cyclohexyl]butyramide (I), b. N-butyl-[4-cis-propoxy-4-trans-(p-trifluoromethylphenyl)cyclohexyl]amine hydrochloride (I), c. 4'-fluoro-4-{[4-cis-propoxy-4-trans-(p-trifluoromethylphenyl)cyclohexyl]-butylamino}butyrophenone hydrochloride (I), 4. a. N-[4-cis-butoxy-4-trans-(2,5-diethylphenyl)cyclohexyl]acetamide (I), b. N-ethyl-[4-cis-butoxy-4-trans-(2,5-diethylphenyl)cyclohexyl]amine hydrochloride (I), c. 4'-fluoro-4-{[4-cis-butoxy-4-trans-(2,5-diethylphenyl)cyclohexyl]ethylamino}butyrophenone hydrochloride (I), 5. a. N-{[4-cis-butoxy-4-trans-(3-chloro-5-fluoro)-phenyl]cyclohexyl}propionamide (I), b. N-propyl-{[4-cis-butoxy-4-trans-(3-chloro-5-fluoro)phenyl]cyclohexyl}amine hydrochloride (I), c. 4'-fluoro-4-{[4-cis-butoxy-4-trans-(3-chloro-5-fluorophenyl)cyclohexyl]propylamino}butyrophenone hydrochloride (I), and the like.

Following the procedure of Example 43(c) but substituting an acid addition salt of another N-alkyl-[4-cis-alkoxy-4-trans-(substituted phenyl) cyclohexyl]amine (I) as starting material and the 2,2-dimethyl-1,3-propanediol ketal of another ω-haloalkanaryl ketone, such as 1. N-ethyl-{[4-cis-propoxy-4-trans-(2-propoxy-6-propyl)-phenyl]cyclohexyl}amine hydrochloride (I) and the 2,2-dimethyl-1,3-propanediol ketal of 4'-butoxy-4-chlorobutyrophenone, 2. N-butyl-[4-cis-ethoxy-4-trans-(p-trifluoromethylphenyl)cyclohexyl]amine hydrochloride (I) and the 2,2-dimethyl-1,3-propanediol ketal of 4'-bromo-4-chlorobutyrophenone, 3. N-ethyl-{[4-cis-isopropoxy-4-trans-(2-fluoro-5-methyl)phenyl)cyclohexyl}amine hydrochloride (I) and the 2,2-dimethyl-1,3-propanediol ketal of 4-chloro-2'-methylbutyrophenone, and the like, yields, respectively, 1. 4'-butoxy-4-{[4-cis-propoxy-4-trans-(2-propoxy-6-propylphenyl)cyclohexyl]ethylamino}butyrophenone hydrochloride (I), 2. 4'-bromo-4-{[4-cis-ethoxy-4-trans-(p-trifluoromethylphenyl)cyclohexyl]ethylamino}butyrophenone hydrochloride (I), 3. 2'-methyl-4-{[4-cis-isopropoxy-4-trans-(2-fluoro-5-methylphenyl)cyclohexyl]ethylamino}butyrophenone hydrochloride (I), and the like.

EXAMPLE 45

N-[4,4-bis(p-fluorophenyl)butyl][4-trans-(p-fluorophenyl)-4-cis-methoxycyclohexyl]amine hydrochloride (I)

To 1 g. of 4-trans-(p-fluorophenyl)-4-cis-methoxycyclohexylamine hydrochloride (I) (prepared as in Example 33) in 15 ml. of dimethylformamide, 0.2 g. of a 56% dispersion of sodium hydride in mineral oil is added. Following about 15 minutes of stirring, 1.5 g. of potassium carbonate, 0.9 g. of potassium iodide and 1.6 g. of 1,1-bis(p-fluorophenyl)-4-chlorobutane [prepared as in Example CLVIII of U.S. Pat. No. 3,238,216, wherein it is named 1-chloro-4,4-di(4-fluorophenyl)butane] is added. Following about 18 hours of heating at about 95° C., the mixture is dissolved in water and benzene. The organic layer is washed with water and brine and evaporated to dryness. The residue is chromatographed on 150 ml. of silica gel (silicic acid) with elution by ammonia saturated methylene chloride; those fractions found similar by thin layer chromatography (TLC) are combined. A solution of the product in methylene chloride is washed with 2.5N hydrochloric acid and evaporated to dryness. This hydrochloric acid salt is freeze dried from benzene to give N-[4,4-bis(p-fluorophenyl)butyl]-[4-trans-(p-fluorophenyl)-4-cis-methoxycyclohexyl]amine hydrochloride (I).

EXAMPLE 46

N-[4,4-bis(p-fluorophenyl)butyl][4-cis-methoxy-4-trans-(p-methylphenyl)cyclohexyl]-amine hydrochloride (I)

Following the procedure of Example 45 but substituting 4-cis-methoxy-4-trans-(p-methylphenyl)cyclohexylamine hydrochloride (I) (prepared as in Example 34) as starting material, yields N-[4,4-bis(p-fluorophenyl)butyl]-[4-cis-methoxy-4-tras-(p-methylphenyl)cyclohexyl]amine hydrochloride (I).

Following the procedure of Example 45 but substituting an acid addition salt of another 4-cis-alkoxy-4-trans-(substituted phenyl)cyclohexylamine (I) and another 1,1-bis(substituted phenyl)-ω-haloalkane, such as 1. 4-cis-ethoxy-4-trans-[(2-ethoxy-5-fluoro)phenyl]-cyclohexylamine hydrobromide (I) and 1-(p-fluorophenyl)-1-(p-trifluoromethylphenyl)-4-chlorobutane, 2. 4-cis-propoxy-4-trans-(p-trifluoromethylphenyl)-cyclohexylamine hydrochloride (I) and 1,1-bis(p-methylphenyl)-4-chlorobutane, 3. 4-cis-methoxy-4-trans-[(2-methyl-6-propoxy)-phenyl]-cyclohexylamine nitrate (I) and 1,1-bis(m-methoxyphenyl)-4-chlorobutane, 4. 4-cis-butoxy-4-trans-[(2-chloro-5-fluoro)phenyl]-cyclohexylamine hydrochloride (I) and 1,1-bis(p-fluorophenyl)-2-chloroethane, 5. 4-cis-butoxy-4-trans-(2,5-diethylphenyl)cyclohexylamine hydrochloride (I) and 1,1-bis(p-ethoxyphenyl)-2-chloroethane, and the like, yields, respectively, 1. N-[4-(p-fluorophenyl)-4-(p-trifluoromethylphenyl)]-butyl-[4-cis-ethoxy-4-trans-(2-ethoxy-5-fluorophenyl)cyclohexyl]amine hydrobromide (I), 2. N-[4,4-bis(p-methylphenyl)]butyl-[4-cis-propoxy-4-trans-(p-trifluoromethylphenyl) cyclohexyl]amine hydrochloride (I), 3. N-[4,4-bis(m-methoxyphenyl)butyl]-[4-cis-methoxy-4-trans-(2-methyl-6-propoxyphenyl) cyclohexyl]amine nitrate (I), 4. N-[4,4-bis(p-fluorophenyl)]ethyl-[4-cis-butoxy-4-trans-(2-chloro-5-fluorophenyl) cyclohexyl]amine hydrochloride (I), 5. N-[4,4-bis(p-ethoxyphenyl)]ethyl-[4-cis-butoxy-4-trans-(2,5-diethylphenyl)cyclohexyl]amine hydrochloride (I), and the like.

EXAMPLE 47

4-cis-(p-fluorophenyl)-4-trans-methoxycyclohexanol and
4-trans-(p-fluorophenyl)-4-cis-methoxycyclohexanol A mixture of 5 g. (0.0225 mole) of 4-methoxy-4-(p-fluorophenyl) cyclohexanone (prepared as in Example 27) and 2.5 g. of sodium borohydride in 100 ml. of ethanol is stirred at room temperature for about 4 hours. The solvent is removed under vacuum and the residue dissolved in ether and water. The organic layer is washed with water and brine and evaporated to dryness. The residue is chromatographed on 500 ml. of silica gel with elution by 10% acetone: 90% methylene chloride to give, first, 0.4 g. of oil shown by nuclear magnetic resonance (NMR) data to be the axial 4-cis-(p-fluorophenyl)-4-trans-methoxycyclohexanol, followed by the crystalline equatorial isomeric 4-trans-(p-fluorophenyl)-4-cis-methoxycyclohexanol. The latter is recrystallized from Skellysolve B to give 3.94 g. (78%) of solid, melting at 82° to 85° C. and has the composition appearing immediately below.

Anal. Calcd. for $C_{13}H_{17}FO_2$: C, 69.69; H, 7.64. Found: C, 69.93; H, 7.61.

EXAMPLE 48

4-trans-methoxy-4-cis-(p-methylphenyl)cyclohexanol
and
4-cis-methoxy-4-trans-(p-methylphenyl)cyclohexanol To a solution of 2 g. (9.2 mmole) of 4-methoxy-4-(p-methylphenyl) cyclohexanone (prepared as in Example 28) in 40 ml. of ethanol, 1 g. of sodium borohydride is added. At the end of about 4 hours the solvent is removed under vacuum and the resulting residue dissolved in ether and water. The organic layer is washed with water and brine and evaporated to dryness. The oil that remains is chromatographed on 200 ml. of silica gel with elution by 20% acetone: Skellysolve B to give, first, 0.22 g. of a compound shown (by NMR data) to be axial 4-trans-methoxy-4-cis-(p-methylphenyl) cyclohexanol, followed by a crystalline product, which on recrystallization from petroleum ether gives 1.4 g. of solid melting at 60° to 62° C. and shown (by NMR data) to be the equatorial isomeric 4-cis-methoxy-4-trans-(p-methylphenyl) cyclohexanol, having the elemental analysis appearing immediately below.

Anal. Calcd. for $C_{14}H_{20}O_2$: C, 76.32; H, 9.15. Found: C, 76.55; H, 9.20.

On a larger scale, 5.51 g. of 4-methoxy-4-(p-methylphenyl)cyclohexanone is reduced as in Example 48 to 4.47 g. (80% yield) of 4-cis-methoxy-4-trans-(p-methylphenyl)cyclohexanol, having a melting point of 57° to 60° C.

Following the procedure of Example 48 but substituting other starting materials, such as 1. 4-methoxy-4-(o-methylphenyl)cyclohexanone,
2. 4-methoxy-4-(m-methylphenyl)cyclohexanone,
3. 4-methoxy-4-(m-trifluoromethylphenyl)cyclohexanone, and the like,
yields, respectively, 1. 4-trans-methoxy-4-cis-(o-methylphenyl)cyclohexanol and 4-cis-methoxy-4-trans-(o-methylphenyl)cyclohexanol, melting point 62° to 66° C. and Anal. Calcd. for $C_{14}H_{20}O_2$: C, 76.32; H, 9.15. Found: C, 76.33; H, 9.29.

2. 4-trans-methoxy-4-cis-(m-methylphenyl)cyclohexanol and 4-cis-methoxy-4-trans-(m-methylphenyl)cyclohexanol, 3. 4-trans-methoxy-4-cis-(m-trifluoromethylphenyl)-cyclohexanol and 4-cis-methoxy-4-trans-(m-trifluoromethylphenyl)cyclohexanol, and the like.

Following the procedure of Example 48 but substituting other starting materials, such as 1. 4-ethoxy-4-(p-fluorophenyl)cyclohexanone,
2. 4-methoxy-4-[(2-methyl-5-propyl)phenyl]-cyclohexanone,
3. 4-propoxy-4-(m-propylphenyl)cyclohexanone,
4. 4-ethoxy-4-(o-trifluoromethylphenyl)cyclohexanone, 5. 4-butoxy-4-[(3-chloro-5-methyl)phenyl]cyclohexanone, and the like, yields, respectively, 1. 4-trans-(and cis)-ethoxy-4-cis(and trans)-(p-fluorophenyl)cyclohexanol, cyclohexanol,
2. 4-trans-(and cis)-methoxy-4-cis(and trans)-[(2-methyl-6-propyl) phenyl]cyclohexanol,
3. 4-trans(and cis)-propoxy-4-cis(and trans)-(m-propylphenyl) cyclohexanol,
4. 4-trans-(and cis)-ethoxy-4-cis(and trans)-(o-trifluoromethylphenyl) cyclohexanol,
5. 4-trans-(and cis)-butoxy-4-cis(and trans)-[(3-chloro-5-methyl) phenyl]cyclohexanol, and the like.

EXAMPLE 49

4-trans-(p-fluorophenyl)-4-cis-methoxycyclohexanol methanesulfonate

A solution of 3.94 g. (0.0176 mole) of 4-trans-(p-fluorophenyl)-4-cis-methoxycyclohexanol (prepared in Example 47) and 4 ml. of methanesulfonyl chloride in 20 ml. of pyridine is allowed to stand in the cold for about 18 hours. The mixture is poured into water and the precipitated solid collected on a filter. This material is recrystallized from ether: Skellysolve B to give 4.85 g. (91%) of 4-trans-(p-fluorophenyl)-4-cis-methoxycyclohexanol methanesulfonate melting at 89.5° to 93° C.

Anal. Calcd. for $C_{14}H_{19}FO_4S$: C, 55.61; H, 6.33. Found: C, 55.26; H, 6.46.

Following the procedure of Example 49 but substituting 4-cis-(p-fluoropheynl)-4-trans-methoxycyclohexanol as starting material, yields 4-cis-(p-fluorophenyl)-4-trans-methoxycyclohexanol methanesulfonate.

EXAMPLE 50

4-cis-methoxy-4-trans-(p-methylphenyl)-cyclohexanol methanesulfonate

To an ice-cooled solution of 5.87 g. (0.026 mole) of 4-cis-methoxy-4-trans-(p-methylphenyl)cyclohexanol (prepared as in Example 48) in 30 ml. of pyridine, 6 ml. of methanesulfonyl chloride is added. Following about 17 hours of standing in the cold, the mixture is diluted with ice and water. The gum that precipitates is extracted with ether and the extract washed successively with water, ice-cold 2.5N hydrochloride acid, aqueous sodium bicarbonate solution and brine. The solution is evaporated to dryness to give 7.95 g. (99%) of 4-cis-methoxy-4-trans-(p-methylphenyl)-cyclohexanol methanesulfonate as a viscous oil.

Following the procedure of Example 50 but substituting 4-trans-methoxy-4-cis-(p-methylphenyl)cyclohexanol as starting material, yields 4-trans-methoxy-4-cis-(p-methyl-phenyl)cyclohexanol methanesulfonate.

Following the procedure of Example 50 but substituting other starting materials, such as 1. 4-cis-methoxy-4-trans-(o-methylphenyl)cyclohexanol,
2. 4-cis-methoxy-4-trans-(m-methylphenyl)cyclohexanol,
3. 4-cis-methoxy-4-trans-(m-trifluoromethylphenyl)-cyclohexanol, and the like, yields, respectively, 1. 4-cis-methoxy-4-trans-(o-methylphenyl)cyclohexanol methanesulfonate, melting point 87° to 90° C. and Anal. Calcd. for $C_{15}H_{22}O_4S$: C, 60.38; H, 7.42. Found: C, 60.34; H, 7.57.

2. 4-cis-methoxy-4-trans-(m-methylphenyl)cyclohexanol methanesulfonate, m.p. 69° to 74° C. and Anal. Calcd. for $C_{15}H_{22}O_4S$: C, 60.38; H, 7.42. Found: C, 60.38; H, 7.23.

3. 4-cis-methoxy-4-trans-(m-trifluoromethylphenyl)-cyclohexanol methanesulfonate, m.p. 64° to 67° C. and Anal. Calcd. for $C_{15}H_{19}F_3O_4S$: C, 51.13; H, 5.43. Found: C, 51.55; H, 5.68.

and the like.

Following the procedures of Example 50 and the paragraph thereafter, but substituting other starting materials and other alkyl (or aryl) sulfonyl halides, such as 1. 4-cis-(and trans)-butoxy-4-trans(and cis)-(m-chlorophenyl) cyclohexanol and ethanesulfonyl bromide, 2. 4-cis-(and trans)-ethoxy-4-trans(and cis)-[(2-fluoro-5-methyl) phenyl]cyclohexanol and propanesulfonyl fluoride, 3. 4-cis(and trans)-methoxy-4-trans(and cis)-[(5-methyl-2-propyl) phenyl]cyclohexanol and α-naphthalenesulfonyl chloride, 4. 4-cis(and trans)-propoxy-4-trans(and cis)-(p-trifluoromethylphenyl)cyclohexanol and p-toluenesulfonyl chloride, and the like, yields, respectively, 1. 4-cis(and trans)-butoxy-4-trans(and cis)-(m-chlorophenyl)cyclohexanol ethanesulfonate, 2. 4-cis(and trans)-ethoxy-4-trans(and cis)-[(2-fluoro-5-methyl) phenyl]cyclohexanol propanesulfonate, 3. 4-cis(and trans)-methoxy-4-trans(and cis)-[(5-methyl-2-propyl)phenyl]cyclohexanol α-naphthalenesulfonate, 4. 4-cis(and trans)-propoxy-4-trans(and cis)-(p-trifluoromethylphenyl)cyclohexanol p-toluenesulfonate, and the like.

EXAMPLE 51

4-cis-(p-fluorophenyl)-4-trans-methoxycyclohexylamine hydrochloride (I)

A mixture of 4.85 g. (0.0165 mole) of 4-trans-(p-fluorophenyl)-4-cis-methoxycyclohexanol methanesulfonate (prepared as in Example 49) and 5 g. of sodium azide in 50 ml. of dimethylformamide is heated for about 17 hours at about 90° C. The solvent is then removed under vacuum and the residue dissolved in water and benzene. The organic layer is washed with water and brine and then evaporated to dryness to give 4-cis-(p-fluorophenyl)-4-trans-methoxycyclohexan-1-ylazide. A solution of this compound in 70 ml. of tetrahydrofuran is added in the course of about 40 minutes to 1 g. of lithium aluminum hydride in 10 ml. of tetrahydrofuran. The mixture is stirred at room temperature for about 5 hours, cooled in ice and successively treated with 1 ml. of water, 1 ml. of 15% aqueous sodium hydroxide solution and 3 ml. of water. The inorganic precipitate is removed by filtration and the filtrate evaporated to dryness. A solution of the residue in ether is treated with 4 ml. of 4.9N hydrochloric acid in ether. The resulting precipitate is recrystallized (without heat) from methanol:ether to give 3.63 g. (82%) of 4-cis-(p-fluorophenyl)-4-transmethoxycyclohexylamine hydrochloride (I), having a melting point of 195° C. (with decomposition).

Anal. Calcd. for $C_{13}H_{19}ClFNO.1/2H_2O$: C, 58.09; H, 7.50; N, 5.21. Found: C, 58.68; H, 7.91; N, 5.27.

Heating the hydrate in a dessicator at about 70° C. at 15 mm. Hg for about 72 hours gives pure 4-cis-(p-fluorophenyl)-4-trans-methoxycyclohexylamine hydrochloride (I).

EXAMPLE 52

4-trans-methoxy-4-cis-(p-methylphenyl)-cyclohexylamine hydrochloride (I)

A mixture of 8.27 g. (0.026 mole) of 4-cis-methoxy-4-trans-(p-methylphenyl)cyclohexanol methanesulfonate (prepared as in Example 50) and 8.3 g. of sodium azide in 80 ml. of dimethylformamide is heated for about 17 hours at about 90° C. The solvent is then removed under vacuum and the residue dissolved in benzene and water. The organic layer is washed with water and brine and evaporated to dryness to give 4-trans-methoxy-4-cis-(p-methylphenyl)-cyclohexan-1-ylazide. A solution of this oily compound in 80 ml. of tetrahydrofuran is added with good stirring in the course of about 40 minutes to 1.5 g. of lithium aluminum hydride in 15 ml. of tetrahydrofuran. The mixture is stirred at room temperature for about 5 hours, cooled in ice and successively treated with 1.5 ml. water, 1.5 ml. of 15% aqueous sodium hydroxide solution and 4.5 ml. of water. The inorganic precipitated gel is removed by filtration and the filtrate evaporated to dryness. The residue is dissolved in ether and treated with a small volume of 4.9N hydrochloric acid in ether. The resulting precipitate is recrystallized from methanol:ether (without heat) to give 5 g. (76%) of 4-trans-methoxy-4-cis-(p-methylphenyl)cyclohexylamine hydrochloride (I), having a melting point above 300° C.

Anal. Calcd. for $C_{14}H_{22}ClNO$: C, 65.73; H, 8.67; N, 5.48. Found: C, 65.71; H, 8.67; N, 5.43.

The mixed melting point of this compound with its isomer, 4-cis-methoxy-4-trans-(p-methylphenyl)cyclohexylamine hydrochloride (I), is 180° to 190° C. (with decomposition).

Following the procedure of Example 52 but substituting other starting materials, such as 1. 4-cis-methoxy-4-trans-(o-methylphenyl)cyclohexanol methanesulfonate, 2. 4-cis-methoxy-4-trans-(m-methylphenyl)cyclohexanol methanesulfonate, 3. 4-cis-methoxy-4-trans-(m-trifluoromethylphenyl)-cyclohexanol methanesulfonate, and the like, yields, respectively, 1. 4-trans-methoxy-4-cis-(o-methylphenyl)cyclohexylamine hydrochloride (I), melting point 208° to 209° C. and Anal. Calcd. for $C_{14}H_{22}ClNO$: C, 65.73; H, 8.67; N, 5.48. Found: C, 65.65; H, 8.83; N, 5.51.

2. 4-trans-methoxy-4-cis-(m-methylphenyl)cyclohexylamine hydrochloride (I), m.p. 163° to 165° C. and Anal. Calcd. for $C_{14}H_{22}ClNO$: C, 65.73; H, 8.67; N, 5.48. Found: C, 65.78; H, 9.17; N, 5.36.

3. 4-trans-methoxy-4-cis-(m-trifluoromethylphenyl)-cyclohexylamine hydrochloride (I), m.p. 184° to 186° C. and Anal. Calcd. for $C_{14}H_{19}ClF_3NO$: C, 54.28; H, 6.18; N, 4.52. Found: C, 53.98; H, 6.01; N, 4.51.

and the like.

Following the procedure of Example 52 but substituting other starting materials, such as 1. 4-cis-methoxy-4-trans-(m-propylphenyl)cyclohexanol ethanesulfonate, 2. 4-cis-butoxy-4-trans-(o-chlorophenyl)cyclohexanol propanesulfonate, 3. 4-cis-ethoxy-4-trans-[(2-ethyl-5-fluoro)phenyl]-cyclohexanol benzenesulfonate, 4. 4-cis-propoxy-4-trans-(p-trifluoromethylphenyl)-cyclohexanol α-naphthalenesulfonate, 5. 4-cis-butoxy-4-trans-[(3-ethyl-6-methyl)phenyl]-cyclohexanol p-toluenesulfonate, and the like, yields, respectively, 1. 4-trans-methoxy-4-cis-(m-propylphenyl)cyclohexylamine hydrochloride (I), 2. 4-trans-butoxy-4-cis-(o-chlorophenyl)cyclohexylamine hydrochloride (I), 3. 4-trans-ethoxy-4-cis-[(2-ethyl-5-fluoro)phenyl]-cyclohexylamine hydrochloride (I), 4. 4-trans-propoxy-4-cis-(p-trifluoromethylphenyl)-cyclohexylamine hydrochloride (I), 5. 4-trans-butoxy-4-cis-[(5-ethyl-2-methyl)phenyl]-cyclohexylamine hydrochloride (I), and the like.

EXAMPLE 53

1-[4-trans-methoxy-4-cis-(p-methylphenyl)-cyclohexyl]piperidine p-toluenesulfonate (I)

To 2.5 g. (9.7 mmole) of 4-trans-methoxy-4-cis-(p-methylphenyl)cyclohexylamine hydrochloride (I) (prepared as in Example 52) in 40 ml. of ethanol, 2.5 ml. of 4.18N sodium methoxide in methanol is added. Following about 30 minutes of stirring, 3.08 g. (1.45 ml.) of 1,5-diiodopentane and 2.56 g. of potassium iodide is added and the mixture heated at reflux for about 17 hours. The solvent is removed under vacuum and the residue dissolved in water and ether. The organic layer is washed with water and brine and evaporated to dryness. To a solution of the oily residue in ether, 1.8 g. of p-toluenesulfonic acid in ether is added. The resulting solid is collected on a filter and recrystallized twice from methylene chloride:ethyl acetate to give 2.66 g. (58%) of 1-[4-trans-methoxy-4-cis-(p-methylphenyl)-cyclohexyl]piperidine p-toluenesulfonate (I), having a melting point of 180° C. (with decomposition).

Anal. Calcd. for $C_{26}H_{37}NO_2S$: C, 67.94; H, 8.11; N, 3.05. Found: C, 67.90; H, 8.39; N, 2.99.

Following the procedure of Example 53 but substituting other starting materials, such as 1. 4-trans-methoxy-4-cis-(o-methylphenyl)cyclohexylamine hydrochloride (I), 2. 4-trans-methoxy-4-cis-(m-methylphenyl)cyclohexylamine hydrochloride (I), and the like, yields, respectively, 1. 1-[4-trans-methoxy-4-cis-(o-methylphenyl)cyclohexyl]piperidine p-toluenesulfonate (I), melting point 171° to 172° C. and Anal. Calcd. for $C_{26}H_{37}NO_2S$: C, 67.94; H, 8.11; N, 3.05. Found: C, 68.17; H, 8.14; N, 3.03.

2. 1-[4-trans-methoxy-4-cis-(m-methylphenyl)-cyclohexyl]piperidine p-toluenesulfonate (I), m.p. 182° to 184° c. (with decomposition) and Anal. Calcd. for $C_{26}H_{37}NO_2S$: C, 67.94; H, 8.11; N, 3.05. Found: C, 67.29; H, 8.02; N, 3.01.

and the like.

Following the procedure of Example 53 but substituting ethereal hydrochloric acid for ethereal p-toluenesulfonic acid, yields 1-[4-trans-methoxy-4-cis-(p-methylphenyl)-cyclohexyl]piperidine hydrochloride (I).

Following the procedures of the immediately preceding paragraph and of Example 53, but substituting other starting materials, such as 1. 4-cis-(p-fluorophenyl)-4-trans-methoxycyclohexyl-amine hydrochloride (I), 2. 4-trans-propoxy-4-cis-(m-trifluoromethylphenyl)-cyclohexylamine hydrochloride (I), 3. 4-trans-butoxy-4-cis-[(5-butyl-2-fluoro)phenyl]-cyclohexylamine hydrochloride (I), 4. 4-trans-4-cis-ethoxy-[(2-ethyl-5-methyl)phenyl]-cyclohexylamine hydrochloride (I), and the like, yields, respectively, 1. 1-[4-cis-(p-fluorophenyl)-4-trans-methoxycyclohexyl]piperidine hydrochloride (I), 2. 1-[4-trans-propoxy-4-cis-(m-trifluoromethylphenyl)-cyclohexyl]piperidine hydrochloride (I), 3. 1- 4-trans-butoxy-4-cis-[(5-butyl-2-fluoro)-phenyl]-cyclohexyl piperidine hydrochloride (I), 4. 1- 4-trans-4-cis-ethoxy-[(2-ethyl-5-methyl)-phenyl]-cyclohexyl piperidine hydrochloride (I), and the like,

EXAMPLE 54

1-[4-cis-(p-fluorophenyl)-4-trans-methoxycyclohexyl]pyrrolidine hydrochloride (I)

Following the procedure of Example 37 but substituting 4-cis-(p-fluorophenyl)-4-trans-methoxycyclohexylamine hydrochloride (I) (prepared as in Example 51) as starting material, yields 1-[4-cis-(p-fluorophenyl)-4-trans-methoxycyclohexyl]pyrrolidine hydrochloride (I).

EXAMPLE 55

1-[4-trans-methoxy-4-cis-(p-methylphenyl)-cyclohexyl]pyrrolidine hydrochloride (I)

Following the procedure of Example 38 but substituting 4-trans-methoxy-4-cis-(p-methylphenyl)cyclohexylamine hydrochloride (I) (prepared as in Example 52) as starting material, yields 1-[4-trans-methoxy-4-cis-(p-methylphenyl)cyclohexyl]pyrrolidine hydrochloride (I).

Following the procedure of Example 55 but substituting other starting materials, such as 1. 4-trans-ethoxy-4-cis-[(2-ethyl-6-fluoro)phenyl]-cyclohexylamine hydrochloride (I), 2. 4-trans-methoxy-4-cis-[(3-ethyl-5-methyl)-phenyl]-cyclohexylamine hydrochloride (I), 3. 4-trans-butoxy-4-cis-[(2-chloro-5-ethoxy)phenyl]-cyclohexylamine hydrochloride (I), and the like, yields, respectively, 1. 1-{4-trans-ethoxy-4-cis-[(2-ethyl-6-fluoro)-phenyl]-cyclohexyl}pyrrolidine hydrochloride (I), 2. 1-{4-trans-methoxy-4-cis-[(3-ethyl-5-methyl)-phenyl]cyclohexyl pyrrolidine hydrochloride (I), 3. 1-{4-trans-butoxy-4-cis-[(2-chloro-5-ethoxy)-phenyl]-cyclohexyl}pyrrolidine hydrochloride (I), and the like.

EXAMPLE 56

1-[4-cis-(p-fluorophenyl)-4-transmethoxycyclohexyl]-hexamethyleneimine hydrochloride (I)

Following the procedure of Example 39 but substituting 4-cis-(p-fluorophenyl)-4-trans-methoxycyclohexylamine hydrochloride (I) (prepared as in Example 51) as starting material, yields 1-[4-cis-(p-fluorophenyl)-4-trans-methoxycyclohexyl]hexamethyleneimine hydrochloride (I).

EXAMPLE 57

1-[4-trans-methoxy-4-cis-(p-methylphenyl)-cyclohexyl]hexamethyleneimine hydrochloride (I)

Following the procedure of Example 40 but substituting 4-trans-methoxy-4-cis-(p-methylphenyl)cyclohexylamine hydrochloride (I) (prepared as in Example 52) as starting material, yields 1-[4-trans-methoxy-4-cis-(p-methylphenyl)-cyclohexyl]hexamethyleneimine hydrochloride (I).

Similarly, employing their other dihaloalkanes with appropriate modifications of the procedures described in Examples 53 through 57, yields representative 1-[4-transalkoxy-4-cis-(substituted phenyl)cyclohexyl]single ring unsubstituted and monosubstituted heterocyclic compounds (e.g., piperidines, pyrrolidines, hexamethyleneimines, morpholines and piperazines), such as 1-[4-trans-ethoxy-4-cis-(m-ethylphenyl)cyclohexyl]-3-methylpiperidine hydrochloride (I), 1-[4-trans-butoxy-4-cis-(p-chlorophenyl)cyclohexyl]-3-propylpyrrolidine hydrochloride (I), 1-{4-trans-butoxy-4-cis-[(3-chloro-5-ethoxy)phenyl]cyclohexyl}-3-ethoxyhexamethyleneimine hydrochloride (I), 1-[4-trans-propoxy-4-cis-(p-trifluoromethylphenyl)cyclohexyl]-morpholine hydrochloride (I), 1-{[4-trans-ethoxy-4-cis-[(5-ethyl-2-fluoro)]phenyl]-cyclohexyl}-2-ethyl-morpholine hydrochloride (I), 1-{4-trans-propoxy-4-cis-[(2,4,6-tripropyl)phenyl]cyclohexyl}piperazine hydrochloride (I), and the like.

EXAMPLE 58

4'-fluoro-4-{[4-cis-(p-fluorophenyl)-4-transmethoxycyclohexyl]amino}butyrophenone hydrohydrochloride (I)

To a solution of 1.96 g. (7.5 mmole) of 4-cis-(p-fluorophenyl)-4-trans-methoxycyclohexylamine hydrochloride (I) (prepared as in Example 51) in 35 ml. of dimethylformamide, 0.32 g. of 57% sodium hydride is added. Following about 1 hour of stirring, 1.29 g. of potassium iodide, 2.15 g. of potassium carbonate and 1.92 g. of the 2,2-dimethyl-1,3-propanediol ketal of 4-chloro-4'-fluorobutyophenone are added. The mixture is stirred for about 17 hours at about 90° C. and the solvent then removed under vacuum. The residue is dissolved in water and benzene and the organic layer washed with water and brine, then evaporated to dryness. The residue is dissolved in 30 ml. of methanol and 15 ml. of 2.5N hydrochloric acid added. After stirring for about 1 hour most of the methanol is removed under vacuum and the solid recovered by filtration. This is recrystallized from methanol:ether (without heating) to give 1.56 g. (48%) of 4'-fluoro-4-{[5-cis-(p-fluorophenyl)-4-methoxycyclohexyl]amino}butyrophenone hydrochloride (I), melting at 193° to 195° C. (with decomposition).

Anal. Calcd. for $C_{23}H_{28}ClF_2NO_2$: C, 65.16; H, 6.66; N, 3.30. Found: C, 65.04; H, 6.65; N, 3.26.

EXAMPLE 59

4'-fluoro-4-{[4-trans-methoxy-4-cis-(p-methylphenyl)-cyclohexyl]amino}butyrophenone hydrochloride (I)

To a solution of 2.5 g. (9.7 mmole) of 4-trans-methoxy-4-cis-(p-methylphenyl)cyclohexylamine hydrochloride (I) (prepared as in Example 52) in 45 ml. of dimethylformamide, 0.41 g. of 57% sodium hydride is added. Following about 1 hour of stirring, 1.65 g. of potassium iodide, 2.76 g. of potassium carbonate and 2.46 g. of the 2,2-dimethyl-1,3-propanediol ketal of 4-chloro-4'-fluorobutyrophenone are added. The mixture is stirred at about 90° C. for about 17 hours and the solvent removed under vacuum. The residue is dissolved in water and benzene and the organic layer washed with water and brine, then evaporated to dryness. The residue is dissolved in 30 ml. of methanol and 15 ml. of 2.5N hydrochloric acid added. following about 1 hour of stirring, most of the methanol is removed under vacuum and the solid recovered by filtration. This is recrystallized from methanol:ether (without heating) to give 1.8 g. (45%) of 4'-fluoro-4-{[4-trans-methoxy-4-cis-(p-methylphenyl)-cyclohexyl]amino}butyrophenone hydrochloride (I), having a melting point of 184° to 185° c. (with decomposition).

Anal. Calcd. for $C_{24}H_{31}ClFNO_2$: C, 68.64; H, 7.44; N, 3.34. Found: C, 68.66; H, 7.84; N, 3.71.

Following the procedure of Example 59 but substituting other starting materials, such as 1. 4-trans-methoxy-4-cis-(o-methylphenyl)cyclohexylamine hydrochloride (I),
2. 4-trans-methoxy-4-cis-(m-methylphenyl)cyclohexylamine hydrochloride (I),
3. 4-trans-methoxy-4-cis-(m-trifluoromethylphenyl)-cyclohexylamine hydrochloride (I), and the like, yields, respectively, 1. 4'-fluoro-4-{[4-trans-methoxy-4-cis-(o-methylphenyl)cyclohexyl]amino}butyrophenone hydrochloride (I), melting point 192° to 193° C. and Anal. Calcd. for $C_{24}H_{31}ClFNO_2$: C, 68.64; H, 7.44; N, 3.34. Found: C, 68.35; H, 7.41; N, 3.15.

2. 4'-fluoro-4-{[4-trans-methoxy-4-cis-(m-methylphenyl)cyclohexyl]amino}butyrophenone hydrochloride (I), m.p. 162° to 164° C. and Anal. Calcd. for $C_{24}H_{31}ClFNO_2 \cdot \frac{1}{2}H_2O$: C, 67.19; H, 7.52; H, 3.27. Found: C, 67.50; H, 7.39; N, 3.11.

3. 4'-fluoro-4-{[4-trans-methoxy-4-cis-(m-trifluoromethylphenyl)cyclohexyl]amino}butyrophenone hydrochloride (I), m.p. 176° to 178° C. and Anal. Calcd. for $C_{24}H_{28}ClFNO_2$: C, 60.82; H, 5.95; N, 2.96. Found: C, 60.58; H, 4.97; N, 2.88.

and the like.

Following the procedure of Example 59 but substituting an acid addition salt of another 4-trans-alkoxy-4-cis-(substituted phenyl)cyclohexylamine (I) as starting material and the 2,2-dimethyl-1,3-propanediol ketal of another ω-haloalkanaryl ketone, such as 1. 4-trans-ethoxy-4-cis-[(2-ethyl-6-fluoro)phenyl]-cyclohexylamine hydrochloride (I) and the 2,2-dimethyl-1,3-propanediol ketal of 4'-bromo-4-chlorobutyrophenone,
2. 4-trans-methoxy-4-cis-[(2-methyl-6-ethyl)-phenyl]-cyclohexylamine hydrobromide (I) and the 2,2-dimethyl-1,3-propanediol ketal of 4-chloro-4'-methoxybutyrophenone,
3. 4-trans-butoxy-4-cis-(2,5-difluorophenyl)cyclohexylamine nitrate (I) and the 2,2-dimethyl-1,3-propanediol ketal of 3',4-dichlorobutyrophenone,
4. 4-trans-butoxy-4-cis-[(3-chloro-5-ethoxy)phenyl]-cyclohexylamine hydrochloride (I) and the 2,2-dimethyl ketal of 3-chloro-4'-ethylpropiophenone,
5. 4-trans-propoxy-4-cis-(p-trifluoromethylphenyl)-cyclohexylamine hydrochloride (I) and the 2,2-dimethyl ketal of 5-chloro-4'-methylvalerophenone, and the like, yields, respectively, 1. 4'-bromo-4-{[4-trans-ethoxy-4-cis-(2-ethyl-6-fluorophenyl)cyclohexyl]amino}butyrophenone hydrochloride (I), 2. 4-methoxy-4-{[4-trans-methoxy-4-cis-(2-methyl-6-ethylphenyl)cyclohexyl]amino}butyrophenone hydrobromide (I), 3. 3'-chloro-4-{[4-trans-butoxy-4-cis-(2,5-difluorophenyl)cyclohexyl]amino}butyrophenone nitrate (I), 4. 4'-ethyl-3-{[4-trans-butoxy-4-cis-(3-chloro-5-ethoxyphenyl)cyclohexyl]amino}propiophenone hydrochloride (I), 5. 4'-methyl-5-{[4-trans-propoxy-cis-(p-trifluoromethylphenyl)cyclohexyl]amino}valerophenone hydrochloride (I), and the like.

EXAMPLE 60

4'-fluoro-4-{[4-cis-(p-fluorophenyl)-4-trans-methoxycyclohexyl]methylamino}butyrophenone hydrochloride (I)

a. N-[4-cis-(p-fluorophenyl)-4-trans-methoxycyclohexyl]formamide (I)

A mixture of 2.5 g. of the free base form of 4-cis-(p-fluorophenyl))-4-trans-methoxycyclohexylamine hydrochloride (I) [obtained by stirring 3 g. of an ether solution of its hydrochloride (prepared as in Example 51) with 2.5 ml. of triethylamine] and 30 ml. of ethyl formate, is heated at reflux for about 40 hours. The resulting solution is evaporated to dryness and the residue recrystallized from benzene to give N-[4-cis-(p-fluorophenyl)-4-trans-methoxycyclohexyl]formamide (I).

Following the procedure of (a), above, but substituting other esters for ethyl formate, such as ethyl acetate, methyl propionate and the like yields, respectively, N-[4-cis-(p-fluorophenyl)-4-trans-methoxycyclohexyl]acetamide (I), N-[4-cis-(p-fluorophenyl)-4-trans-methoxycyclohexyl]-propionamide (I), and the like.

b. N-methyl-[4-cis-(p-fluorophenyl)-4-trans-methoxycyclohexyl]amine hydrochloride (I)

A solution of 2.5 g. of N-methyl-[4-cis-(p-fluorophenyl)-4-trans-methoxycyclohexyl]formamide (I) [obtained as in (a), above] in 75 ml. of tetrahydrofuran is added to a well stirred suspension of 0.65 g. of lithium aluminum hydride in 15 ml. of tetrahydrofuran. After heating this mixture for about 4 hours it is cooled in ice, and 0.6 ml. of water, 0.6 ml. of 15% aqueous sodium hydroxide solution are added successively. The solid that precipitates is removed by filtration and the filtrate evaporated to dryness. The residue is dissolved in ether and treated with a small excess of 3.6N ethereal hydrogen chloride. The solid that precipitates is recrystallized from methylene chloride: ethyl acetate to give N-methyl-[4-cis-(p-fluorophenyl)-4-trans-methoxycyclohexyl]amine hydrochloride (I).

Following the procedure of (b), above, but substituting N-[4-cis-(p-fluorophenyl)-4-trans-methoxycyclohexyl]-acetamide (I), N-[4-cis-(p-fluorophenyl)-4-trans-methoxycyclohexyl]butyramide (I), and the like, yields, respectively, N-ethyl-[4-cis-(p-fluorophenyl)-4-trans-methoxycyclohexyl]amine hydrochloride (I), N-butyl-[4-cis-(p-fluorophenyl)-4-trans-methoxycyclohexyl]amine hydrochloride (I), and the like.

c. 4'-fluoro-4-{[4-cis-(p-fluorophenyl)-4-trans-methoxycyclohexyl]methylamino}butyrophenone hydrochloride (I)

To a suspension of 2 g. of N-methyl-[4-cis-(p-fluorophenyl)-4-trans-methoxycyclohexyl]amine hydrochloride (I) [prepared as in (b), above] in 30 ml. of dimethylformamide, 0.4 g. of sodium hydride (56% in mineral oil) is added. Following about 30 minutes of stirring there is added successively, 2.6 g. of potassium carbonate, 1.6 g. of potassium iodide and 2.5 g. of the 2,2-dimethyl-1,3-propanediol ketal of 4-chloro-4'-fluorobutyrophenone. The mixture is stirred at about 90° C. for about 18 hours, allowed to cool and diluted with benzene and water. The organic layer is washed with water and brine and taken to dryness. A solution of the residue in 70 ml. of methanol and 35 ml. of 2.5N hydrochloric acid is stirred for about 2 hours at room temperature. The methanol is then removed under vacuum and the residue extracted with methylene chloride. The organic layer is washed once with 2.5N hydrochloric acid and taken to dryness. The residual solid is recrystallized twice from methylene chloride-:ethyl acetate to give 4'-fluoro-{[4-cis-(p-fluorophenyl)-4-trans-methoxycyclohexyl]methylamino}butyrophenone hydrochloride (I).

Following the procedure of (c), above, but substituting N-ethyl-[4-cis-(p-fluorophenyl)-4-trans-methoxycyclohexyl]-amine hydrochloride (I), N-butyl-[4-cis-(p-fluorophenyl)-4-trans-methoxycyclohexyl]amine hydrochloride (I), and the like, yields, respectively, 4'-fluoro-4-{[4-cis-(p-fluorophenyl)-4-trans-methoxycyclohexyl]ethylamino}-butyrophenone hydrochloride (I), 4'-fluoro-4-{[4-cis-(p-fluorophenyl)-4-trans-methoxycyclohexyl]butylamino}-butyrophenone hydrochloride (I) and the like.

EXAMPLE 61

4'-fluoro-4-{[4-trans-methoxy-4-cis-(p-methylphenyl)-cyclohexyl]methylamino}-butyrophenone hydrochloride (I)

Following the procedure of Example 60 but substituting the free base form of 4-trans-methoxy-4-cis-(p-methylphenyl)-cyclohexylamine hydrochloride (I) (prepared as in Example 52) as starting material, yields, respectively, (a) N-[4-trans-methoxy-4-cis-(p-methylphenyl)cyclohexyl]formamide (I), (b) N-methyl-[4-trans-methoxy-4-cis-(p-methylphenyl)-cyclohexyl]amine hydrochloride (I) and (c) 4'-fluoro-4-{[4-trans-methoxy-4-cis-(p-methylphenyl)cyclohexyl]methylamino}-butyrophenone hydrochloride (I).

Following the procedures of Examples 60 and 61 but substituting other starting materials and other esters for ethyl formate in (a) of the former example, such as 1. 4-trans-ethoxy-4-cis-[(2-ethyl-6-fluoro)phenyl]-cyclohexylamine hydrochloride (I) and ethyl acetate, 2. 4-trans-methoxy-4-cis-[(3-propoxy-4-propyl)-phenyl]-cyclohexylamine hydrochloride (I) and methyl propionate, 3. 4-trans-butoxy-4-cis-(2,5-diethylphenyl)cyclohexylamine hydrochloride (I) and ethyl butyrate, and the like, yields, respectively, 1 a N-{[4-trans-ethoxy-4-cis-(2-ethyl-6-fluoro)-phenyl]cyclohexyl}acetamide (I), b N-ethyl{[4-trans-ethoxy-4-cis-(2-ethyl-6-fluoro)phenyl]cyclohexyl}amine hydrochloride (I), c 4'-fluoro-4-{[4-trans-ethoxy-4-cis-(2-ethyl-6-fluorophenyl)cyclohexyl]ethylamino}butyrophenone hydrochloride (I), 2 a. N-{[4-trans-methoxy-4-cis-(3-propoxy-4-propyl)phenyl]cyclohexyl}propionamide (I), b. N-propyl-{[4-trans-methoxy-4-cis-(3-propoxy-4-propyl)phenyl]cyclohexyl}amine hydrochloride (I), c. 4'-fluoro-4-{[4-trans-methoxy-4-cis-(3-propoxy-4-propylphenyl)cyclohexyl]-propylamino}butyrophenone hydrochloride (I), 3 a. N-[4-trans-butoxy-4-cis-(2,5-diethylphenyl)cyclohexyl]butyramide hydrochloride (I), b. N-butyl-[4-trans-butoxy-4-cis-(2,5-diethylphenyl)cyclohexyl]amine hydrochloride (I), c. 4'-fluoro-4- [4-trans-butoxy-4-cis-(2,5-diethylphenyl)cyclohexyl]butylamino butyrophenone hydrochloride (I), and the like.

Following the procedure of Example 60(c) but substituting an acid addition salt of another N-alkyl-[4-trans-alkoxy-4-cis-(substituted phenyl)cyclohexyl]amine (I) as starting material and the 2,2-dimethyl-1,3-propanediol ketal of another ω-haloalkanaryl ketone, such as 1. N-ethyl-{[4-trans-isobutoxy-4-cis-(2-fluoro-6-propyl)phenyl]cyclohexyl}amine hydrochloride (I) and the 2,2-dimethyl-1,3-propanediol ketal of 4-chloro-2'-ethylbutyrophenone, 2. N-butyl-[4-trans-ethoxy-4-cis-(p-trifluoromethylphenyl)cyclohexyl]amine hydrochloride (I) and the 2,2-dimethyl-1,3-propanediol ketal of 4'-bromo-4-chlorobutyrophenone, and the like, yields, respectively, 1. 2'-ethyl-4-{[4-trans-isobutoxy-4-cis-(2-fluoro-6-propylphenyl)cyclohexyl]ethylamino}butyrophenone hydrochloride (I), 2. 4'-bromo-4-{[4-trans-ethoxy-4-cis-(p-trifluoromethylphenyl)cyclohexyl]butylamino}butyrophenone hydrochloride (I), and the like.

EXAMPLE 62

N-[4,4-bis(p-fluorophenyl)butyl]-[4-cis-(p-fluorophenyl)-4-trans-methoxycyclohexyl]-amine hydrochloride (I)

To 1 g. of 4-cis-(p-fluorophenyl)-4-trans-methoxycyclohexylamine hydrochloride (I) (prepared as in Example 51) in 15 ml. of dimethylformamide, 0.2 g. of a 56% dispersion of sodium hydride in mineral oil is added. Following about 15 minutes of stirring, 1.5 g. of potassium carbonate, 0.9 g. of potassium iodide and 1.6 g. of 1,1-bis(p-fluorophenyl)-4-chlorobutane [prepared as in Example CLVIII of U.S. Pat. No. 3,238,216, wherein it is named 1-chloro-4,4-di(4-fluorophenyl)butane] is added. Following about 18 hours of heating at about 95° C., the mixture is dissolved in water and benzene. The organic layer is washed with water and brine and taken to dryness. The residue is chromatographed on 150 ml. of silica gel (silicic acid) with elution by ammonia saturated methylene chloride; those fractions found similar by thin layer chromatography (TLC) are combined. A solution of the product in methylene chloride is washed with 2.5N hydrochloric acid and taken to dryness. This hydrochloride salt is freeze dried from benzene to give N-[4,4-bis-(p-fluorophenyl)butyl]-4-cis-(p-fluorophenyl)-4-trans-methoxycyclohexylamine hydrochloride (I).

EXAMPLE 63

N-[4,4-bis(p-fluorophenyl)butyl]-[4-trans-methoxy-4-cis-(p-methylphenyl)cyclohexyl]-amine hydrochloride (I)

Following the procedure of Example 62 but substituting 4-trans-methoxy-4-cis-(p-methylphenyl)cyclohexylamine hydrochloride (I) (prepared as in Example 52) as starting material, yields N-[4,4-bis(p-fluorophenyl)butyl]-[4-trans-methoxy-4-cis-(p-methylphenyl)cyclohexyl]amine hydrochloride (I).

Following the procedure of Example 62 but substituting an acid addition salt of another 4-trans-alkoxy-4-cis-(substituted phenyl)cyclohexylamine (I) and another 1,1-bis(substituted phenyl)-ω-haloalkane, such as 1. 4-trans-ethoxy-4-cis-[(2-ethoxy-6-fluoro)phenyl]-cyclohexylamine nitrate (I) and 1-(p-fluorophenyl)-1-(p-trifluoromethylphenyl)-4-chlorobutane, 2. 4-trans-butoxy-4-cis-(2,6-dichlorophenyl)-cyclohexylamine hydrochloride (I) and 1,1-bis(p-methoxyphenyl)-2-chloroethane, 3. 4-trans-propoxy-4-cis-(p-trifluoromethylphenyl)-cyclohexylamine hydrochloride (I) and 1,1-bis(m-chlorophenyl)-4-chlorobutane, and the like, yields, respectively, 1. N-[4-(p-fluorophenyl)-4-(p-trifluoromethylphenyl)]-butyl-[4-trans-ethoxy-4-cis-(2-ethoxy-6-fluorophenyl)-cyclohexyl]amine nitrate (I), 2. N-[4,4-bis(p-methoxyphenyl)]ethyl-[4-trans-butoxy-4-cis-(2,6-dichlorophenyl)cyclohexyl]amine hydrochloride (I), 3. N-[4,4-bis(m-chlorophenyl)]butyl-[4-trans-propoxy-4-cis-(p-trifluoromethylphenyl)cyclohexyl]amine hydrochloride (I) and the like.

I claim:

1. A compound of the formula

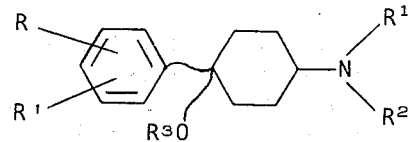

wherein ~ is a generic expression denoting cis and trans stereoconfiguration and mixtures thereof, with the proviso that when the stereoconfiguration of the linkage connecting the cyclohexane ring and $R^3O$ is cis to the amino group, the linkage connecting the cyclohexane and phenyl rings is always trans, and vice versa; R is selected from the group consisting of lower alkyl of 1 through 4 carbon atoms, chlorine, fluorine, bromine, trifluoromethyl, and lower alkoxy of 1 through 4 carbon atoms; R' has the same meaning as R and in addition hydrogen; $R^1$ is selected from the group consisting of hydrogen and lower alkyl of 1 through 4 carbon atoms; $R^2$ is ring monosubstituted aroylalkyl wherein the substituents have the same meaning as R and R', above, aryl is from 6 through 10 carbon atoms and alkyl of from 1 through 4 carbon atoms; and acid addition salts thereof.

2. A compound of claim 1 wherein R is p-fluoro, R' and $R^1$ are hydrogen, $R^2$ is 4-oxo-4-(p-fluorophenyl)-butyl, $R^3O$ is methoxy having cis stereoconfiguration, and the acid addition salt is that of hydrochloric acid, namely, 4'-fluoro-4-{[4-trans-(p-fluorophenyl)-4-cis-methoxycyclohexyl]amino}-butyrophenone hydrochloride.

3. A compound of claim 1 wherein R is p-fluoro, R' and $R^1$ are hydrogen, $R^2$ is 4-oxo-4-(p-fluorophenyl)-butyl, $R^3O$ is methoxy having trans stereoconfiguration, and the acid addition salt is that of hydrochloric acid, namely, 4'-fluoro-4-{[4-cis-(p-fluorophenyl)-4-trans-methoxycyclohexyl]amino}-butyrophenone hydrochloride.

4. A compound of claim 1 wherein R is p-methyl, R' and $R^1$ and hydrogen, $R^2$ is 4-oxo-4-(p-fluorophenyl)-butyl, $R^3O$ is methoxy having cis stereoconfiguration, and the acid addition salt is that of hydrochloric acid, namely, 4'-fluoro-4-{[4-cis-methoxy-4-trans-(p-methylphenyl)cyclohexyl]-amino}butyrophenone hydrochloride.

5. A compound of claim 1 wherein R is p-methyl, R' and $R^1$ are hydrogen, $R^2$ is 4-oxo-4-(p-fluorophenyl)-butyl, $R^3O$ is methoxy having trans stereoconfiguration is trans and the acid addition salt is that of hydrochloric acid, namely, 4'-fluoro-4-{[4-trans-methoxy-4-cis-(p-methylphenyl)cyclohexyl]amino}butyrophenone hydrochloride.

6. A compound of claim 1 wherein R is m-methyl, R' and $R^1$ are hydrogen, $R^2$ is 4-oxo-4-(p-fluorophenyl)-butyl, $R^3O$ is methoxy having cis stereoconfiguration, and the acid addition salt is that of hydrochloric acid, namely, 4'-fluoro-4-{[4-cis-methoxy-4-trans-(m-methylphenyl)cyclohexyl]-amino}butyrophenone hydrochloride.

7. A compound of claim 1 wherein R is m-methyl, R' and $R^1$ are hydrogen, $R^2$ is 4-oxo-4-(p-fluorophenyl)-butyl, $R^3O$ is methoxy having trans stereoconfiguration, and the acid addition salt is that of hydrochloric acid, namely, 4'-fluoro-4-{[4-trans-methoxy-4-cis-(m-methylphenyl)cyclohexyl]-butyrophenone}hydrochloride.

8. A compound of claim 1 wherein R is o-methyl, R' and $R^1$ are hydrogen, $R^2$ is 4-oxo-4-(p-fluorophenyl)-butyl, $R^3O$ is methoxy having cis-stereoconfiguration, and the acid addition salt is that of hydrochloric acid, namely, 4'-fluoro-4-{[4-cis-methoxy-4-trans-(o-methylphenyl)cyclohexyl]-butyrophenone}hydrochloride.

9. A compound of claim 1 wherein R is o-methyl, R' and $R^1$ are hydrogen, $R^2$ is 4-oxo-4-(p-fluorophenyl)-butyl, $R^3O$ is methoxy having trans stereoconfiguration, and the acid addition salt is that of hydrochloric acid, namely, 4'-fluoro-4-{[4-trans-methoxy-4-cis-(o-methylphenyl)cyclohexyl]-butyrophenone}hydrochloride.

10. A compound of claim 1 wherein R is m-trifluoromethyl, R' and $R^1$ are hydrogen, $R^2$ is 4-oxo-4-(p-fluorophenyl)-butyl, $R^3O$ is methoxy having cis stereoconfiguration, and the acid addition salt is that of hydrochloric acid, namely, 4'-fluoro-4-{[4-cis-methoxy-4-trans-(m-trifluoromethylphenyl)-cyclohexyl]amino}butyrophenone hydrochloride.

11. A compound of claim 1 wherein R is m-trifluoromethyl, R' and $R^1$ are hydrogen, $R^2$ is 4-oxo-4-(p-fluorophenyl)-butyl, $R^3O$ is methoxy having trans stereoconfiguration, and the acid addition salt is that of hydrochloric acid, namely, 4'-fluoro-4-{[4-trans-methoxy-4-cis-(m-trifluoromethylphenyl)-cyclohexyl]amino} butyrophenone hydrochloride.

12. A compound of claim 1 wherein R is o-methoxy, R' and $R^1$ are hydrogen, $R^2$ is 4-oxo-4-(p-fluorophenyl)butyl, $R^3O$ is methoxy having cis stereoconfiguration, and the acid addition salt is that of hydrochloric acid, namely, 4'-fluoro-4-{[4-cis-methoxy-4-trans-(o-methoxyphenyl)cyclohexyl]-amino}butyrophenone hydrochloride.

13. A compound of claim 1 wherein R is p-chloro, R' and $R^1$ are hydrogen, $R^2$ is 4-oxo-4-(p-fluorophenyl)-butyl, $R^3O$ is methoxy having cis stereoconfiguration, and the acid addition salt is that of hydrochloric acid, namely, 4'-fluoro-4-{[4-trans-(p-chlorophenyl)-4-cis-methoxycyclohexyl]-amino}butyrophenone hydrochloride.

* * * * *